United States Patent
Oldham et al.

(10) Patent No.: US 7,498,164 B2
(45) Date of Patent: Mar. 3, 2009

(54) INSTRUMENT FOR MONITORING NUCLEIC ACID SEQUENCE AMPLIFICATION REACTION

(75) Inventors: Mark F. Oldham, Los Gatos, CA (US); Eugene F. Young, Marietta, GA (US)

(73) Assignee: Applied Biosystems, LLC, Carlsbad, CA (US)

(*) Notice: Subject to any disclaimer, the term of this patent is extended or adjusted under 35 U.S.C. 154(b) by 646 days.

(21) Appl. No.: 10/456,196

(22) Filed: Jun. 6, 2003

(65) Prior Publication Data

US 2004/0009586 A1 Jan. 15, 2004

Related U.S. Application Data

(63) Continuation-in-part of application No. 10/216,620, filed on Aug. 9, 2002, now Pat. No. 7,008,789, which is a continuation of application No. 09/700,536, filed as application No. PCT/US99/11088 on May 17, 1999, now Pat. No. 6,818,437.

(60) Provisional application No. 60/092,784, filed on Jul. 14, 1998, provisional application No. 60/085,765, filed on May 16, 1998.

(51) Int. Cl.
- C12M 1/34 (2006.01)
- C12M 3/00 (2006.01)
- G01N 21/64 (2006.01)
- G01J 1/58 (2006.01)
- F21V 9/16 (2006.01)

(52) U.S. Cl. .............. 435/288.7; 435/808; 435/303.1; 435/288.4; 435/809; 378/42; 378/45; 422/82.08; 250/483.1; 250/459.1; 250/461.1; 250/461.2; 356/73

(58) Field of Classification Search ............. 435/808, 435/288.7, 809, 303.1, 288.4; 378/42, 45; 422/82.08; 250/483.1, 459.1, 461.2, 461.1; 356/73

See application file for complete search history.

(56) References Cited

U.S. PATENT DOCUMENTS 4,284,897 A    8/1981   Sawamura et al. ...... 250/461 B (Continued)

FOREIGN PATENT DOCUMENTS

DE    196 51 667 A1    9/1997

(Continued)

OTHER PUBLICATIONS

H. W. Sands Corp., *OLED Emitters Selected By Color Emission,* http://www.hwsands.com/productlists/oled_emitters_color_emission.htm (Printed Jan. 10, 2003).

(Continued)

*Primary Examiner*—Willliam H Beisner
*Assistant Examiner*—Nathan A Bowers
(74) *Attorney, Agent, or Firm*—Kilyk & Bowersox, P.L.L.C.

(57) ABSTRACT

An instrument is provided that can monitor nucleic acid sequence amplifications reactions, for example, PCR amplification of DNA and DNA fragments. The instrument includes a multi-notch filter disposed along one or both of an excitation beam path and an emission beam path. Methods are also provided for monitoring nucleic acid sequence amplifications using an instrument that includes a multi-notch filter disposed along a beam path.

28 Claims, 8 Drawing Sheets

U.S. PATENT DOCUMENTS

| | | | |
|---|---|---|---|
| 4,626,684 A | 12/1986 | Landa | 250/328 |
| 4,643,877 A | 2/1987 | Opitz et al. | 422/68 |
| 4,673,289 A | 6/1987 | Gaucher | 356/72 |
| 4,683,202 A | 7/1987 | Mullins | 435/91 |
| 5,073,029 A | 12/1991 | Eberly et al. | 356/432 |
| 5,091,652 A | 2/1992 | Mathies et al. | 250/458.1 |
| 5,169,601 A | 12/1992 | Ohta et al. | 422/73 |
| 5,215,883 A | 6/1993 | Chu | 435/6 |
| 5,241,363 A * | 8/1993 | Garner | 356/326 |
| 5,243,540 A | 9/1993 | Van Albert et al. | 364/500 |
| 5,256,880 A | 10/1993 | Loree et al. | 250/461.1 |
| 5,315,375 A | 5/1994 | Allen | 356/417 |
| 5,355,215 A | 10/1994 | Schroeder et al. | 356/317 |
| 5,371,016 A | 12/1994 | Berndt | 435/291 |
| 5,377,004 A * | 12/1994 | Owen et al. | 356/301 |
| 5,383,023 A | 1/1995 | Walleczek | 356/417 |
| 5,389,544 A | 2/1995 | Sugata et al. | 435/291 |
| 5,475,610 A | 12/1995 | Atwood et al. | 364/500 |
| 5,527,684 A | 6/1996 | Mabile et al. | |
| 5,547,849 A | 8/1996 | Baer et al. | 435/7.24 |
| 5,567,947 A | 10/1996 | Kebabian | 250/458.1 |
| 5,595,708 A | 1/1997 | Berndt | 422/82.06 |
| 5,635,402 A | 6/1997 | Alfano et al. | |
| 5,656,493 A | 8/1997 | Mullis et al. | 435/286.1 |
| 5,672,880 A | 9/1997 | Kain | 250/458.1 |
| 5,736,333 A | 4/1998 | Livak et al. | 435/6 |
| 5,759,781 A | 6/1998 | Ward et al. | 435/6 |
| 5,766,889 A | 6/1998 | Atwood | 435/91.2 |
| 5,779,978 A | 7/1998 | Hartmann et al. | 422/82.05 |
| 5,792,610 A | 8/1998 | Witney et al. | 435/6 |
| 5,846,842 A | 12/1998 | Herron et al. | 436/518 |
| 5,854,684 A | 12/1998 | Stabile et al. | 356/440 |
| 5,863,502 A | 1/1999 | Southgate et al. | 422/58 |
| 5,872,623 A | 2/1999 | Stabile et al. | |
| 5,926,271 A | 7/1999 | Couderc et al. | 356/318 |
| 5,943,129 A | 8/1999 | Hoyt et al. | 356/318 |
| 5,958,349 A * | 9/1999 | Petersen et al. | 422/198 |
| 6,040,940 A | 3/2000 | Kawasaki | 359/389 |
| 6,057,114 A | 5/2000 | Akong et al. | 435/7.21 |
| 6,096,272 A | 8/2000 | Clark et al. | 422/64 |
| 6,197,575 B1 | 3/2001 | Griffith et al. | 435/288.4 |
| 6,252,717 B1 | 6/2001 | Grosskopf | |
| 6,287,871 B1 | 9/2001 | Herron et al. | 436/172 |
| 6,309,601 B1 | 10/2001 | Juncosa et al. | 422/68.1 |
| 6,331,438 B1 | 12/2001 | Aylott et al. | 436/172 |
| 6,337,740 B1 | 1/2002 | Parce | 356/344 |
| 6,352,672 B1 | 3/2002 | Mabile et al. | 422/82.08 |
| 6,364,516 B1 | 4/2002 | Li et al. | 362/553 |
| 6,388,788 B1 | 5/2002 | Harris et al. | 359/196 |
| 6,411,835 B1 | 6/2002 | Modell et al. | 600/407 |
| 6,455,861 B1 * | 9/2002 | Hoyt | 250/458.1 |
| 6,529,275 B2 | 3/2003 | Amirkhanian et al. | 356/413 |
| 6,542,241 B1 * | 4/2003 | Thorwirth et al. | 356/436 |
| 6,686,582 B1 | 2/2004 | Völcker et al. | |
| 6,717,668 B2 * | 4/2004 | Treado et al. | 356/327 |
| 6,818,437 B1 | 11/2004 | Gambini et al. | |
| 7,030,371 B2 * | 4/2006 | Vasic et al. | 250/271 |
| 2001/0033374 A1 | 10/2001 | Hoyt | |
| 2002/0055178 A1 | 5/2002 | Wardlaw | |
| 2002/0060791 A1 | 5/2002 | Srumbo et al. | |
| 2002/0146688 A1 | 10/2002 | Kinjo | |
| 2004/0165256 A1 * | 8/2004 | Teng et al. | 359/359 |

FOREIGN PATENT DOCUMENTS

| | | |
|---|---|---|
| DE | 197 48 211 A1 | 5/1999 |
| EP | 0 065 409 A2 | 11/1982 |
| EP | 0 640 828 A1 | 3/1995 |
| EP | 0640828 A1 * | 3/1995 |
| EP | 0 987 539 A1 | 3/2000 |
| JP | 60-108457 | 6/1985 |
| JP | 63-287177 | 11/1988 |
| JP | 62-16911 | 8/1994 |
| JP | 07-120392 | 5/1995 |
| JP | 07-120393 | 5/1995 |
| JP | 07-163397 | 6/1995 |
| JP | 07-174701 | 7/1995 |
| JP | 09-072843 | 3/1997 |
| JP | 09-166752 | 6/1997 |
| JP | 09-281078 | 10/1997 |
| JP | 10-115781 | 5/1998 |
| JP | 10-115783 | 5/1998 |
| WO | WO 96/05488 | 2/1996 |
| WO | WO 96/07888 | 3/1996 |
| WO | WO 97/34171 | 9/1997 |
| WO | WO 97/46707 | 12/1997 |
| WO | WO 97/46708 | 12/1997 |
| WO | WO 99/60381 | 11/1999 |
| WO | WO 01/35079 A1 | 5/2001 |

OTHER PUBLICATIONS

Hebner et al., Local Tuning of Organic Light-Emitting Diode Color by Dye Droplet Application, *American Institute of Physics*, 1998.

Higuchi et al., Kinetic PCR Analysis: Real-Time Monitoring Of DNA Amplification Reactions, *Bio Technology*, vol. 11, pp. 1026-1030 (1993).

Qui et al., Room Temperature Ultraviolet Emission From an Organic Light-Emitting Diode, *American Institute of Physics* (2001).

Ririe et al., Product Differentiation By Analysis of DNA Melting Curves During the Polymerase Chain Reaction, *Analytical Biochemistry*, vol. 245, pp. 154-160 (1997).

Teresko, Winning Technologies: Organic Light Emitting Diode, *Industry Week*, (Dec. 11, 2000).

Tollefsrud, *Electronic Paper: Organic Light Emitting Diode,* http://komar.cs.stthomas.edu/qm425/01s/Tollefsrud2.htm (Printed Jan. 10, 2003).

Wittwer et al., The LightCycler™:A Microvolume Multisample Fluorimeter with Rapid Temperature Control, *BioTechniques* vol. 22, No. 1, pp. 176-181 (Jan. 1997).

Communication dated Sep. 15, 2008, from European Patent Application No. 08011345.9.

Extended European Search Report dated Aug. 27, 2008, from European Patent Application No. 08011345.9.

Vöcker, et al., "Mikroskopgestützte Fluoreszenz-Photonen-Korrelation," Technisches Messen, vol. 63, No. 4, pp. 128-135, (Apr. 1, 1996).

* cited by examiner

INSTRUMENT FOR MONITORING NUCLEIC ACID SEQUENCE AMPLIFICATION REACTION

CROSS-REFERENCE TO RELATED APPLICATIONS

The present application is a continuation-in-part of U.S. patent application Ser. No. 10/216,620, filed Aug. 9, 2002, now U.S. Pat. No. 7,008,789, which is a continuation of U.S. patent application Ser. No. 09/700,536, filed Nov. 29, 2001, now U.S. Pat. No. 6,818,437, which is a National Phase Application Under 35 U.S.C. § 371 of PCT International Application No. PCT/US99/11088, filed on May 17, 1999, which claims benefit from U.S. Provisional Patent Application No. 60/085,765, filed May 16, 1998, and from U.S. Provisional Patent Application No. 60/092,784, filed Jul. 14, 1998. U.S. patent application Ser. No. 10/370,846, filed Feb. 20, 2003, is a related application. All of the above-identified applications are incorporated herein in their entireties by reference.

FIELD

This teachings relates to biochemical analyses, and particularly to quantitative monitoring of nucleic acid sequence amplification reaction processes.

BACKGROUND

Quantitative measurements can be made on the amount of DNA production during a polymerase chain reaction (PCR) process, to provide measurements of the starting amount and the amount produced. Measurements and computation techniques are taught in U.S. Pat. No. 5,766,889 (Atwood), as well as in the article "Kinetic PCR Analysis: Real-time Monitoring of DNA Amplification Reactions" by Russel Higuchi, et al., Bio/Technology vol. 11, pp. 1026-1030 (September 1993), and in the article "Product Differentiation by Analysis of DNA Melting Curves during the Polymerase Chain Reaction" by Kirk M. Ririe, et al., Analytical Biochemistry vol. 245, pp. 154-160 (1997), which are incorporated herein in their entirety by reference.

There is a need for greater precision during monitoring and measuring PCR and other nucleic acid amplification techniques. Previous instruments that allow real time acquisition and analysis of PCR data can be very basic devices without the required dynamic range, can be without built-in calibration devices, can disallow operation with sample well caps, or can be very expensive.

SUMMARY

According to various embodiments, an optical instrument that includes a multi-notch filter for quantitative monitoring nucleic acid sequence amplification in an amplification apparatus. The instrument can possess improved dynamic range, automatic selection of exposure time to extend dynamic range, automatic adjustment for drift, simplified operation, relatively low cost, and easy changing of optics to accommodate different fluorescent dyes. According to various embodiments, the instrument can be used in monitoring a PCR, isothermal amplification, or other nucleic acid sequence amplification or replication techniques.

According to various embodiments, a instrument is provided that includes an excitation light source, at least one reaction region capable of retaining at least one respective sample that is capable of emitting emission beams along an emission beam path, a multi-notch filter disposed along an excitation beam path between the excitation light source and the at least one reaction region, and a detector arranged along the emission beam path. The at least one reaction region can include a plurality of reaction regions, for example, 96 reaction wells. The instrument can further include a second multi-notch filter disposed along an emission beam path between the at least one reaction region and the detector.

According to various embodiments, and by way of example, an optical instrument including a multi-notch filter is provided for monitoring polymerase chain reaction replication of DNA. The amplification can be in a reaction region or apparatus that includes a well, for example, a thermal cycler block for holding at least one vial containing a suspension of ingredients for the reaction. The ingredients can include a fluorescent dye that fluoresces proportionately in presence of DNA. The instrument is capable of monitoring other nucleic acid sequence amplification reactions, including isothermal amplification reactions.

According to various embodiments, the instrument can include an excitation light source, device for directing light beams, a multi-notch filter, a light detector, and device for processing data signals. The light source can emit a source beam including at least a primary excitation frequency that can cause the dye to fluoresce at an emission frequency. A first device can be disposed to be receptive of the source beam to effect an excitation beam including the excitation frequency. A primary focusing device can be disposed to focus the excitation beam into each suspension such that the primary dye can emit an emission beam including an emission frequency and an intensity representative of a concentration of a target nucleic acid sequence in each suspension. The focusing device can be receptive of and can pass the emission beam. A second device can be disposed to be receptive of the emission beam from the focusing device so as to further pass the emission beam at the emission frequency to another focusing device that can focus the emission beam onto a detector. The detector can generate primary data signals representative of the emission beam and thereby a corresponding concentration of the target nucleic acid sequence in each vial. A processor can be receptive of the primary data signals for computing and displaying the concentration of the target nucleic sequence.

According to various embodiments, the first device and the second device together can include a beam splitter that can be receptive of the source beam to effect the excitation beam, and receptive of the emission beam to pass the emission beam to the detector. The beam splitter can be a multi-notch beam splitter. The block can be configured to hold a plurality of vials. The focusing device can include a corresponding plurality of vial lenses each disposed over a vial. The focusing device can be disposed such that the emission beam can include individual beams associated with each vial. The focusing device can include a field lens, for example, a Fresnel lens. The field lens can be disposed cooperatively with the vial lenses to effect focusing of the excitation beam into each suspension. The field lens can pass the individual beams to the second device, for example, a beam splitter. According to various embodiments, the detector can include an array of photoreceptors receptive of each individual beam to generate corresponding data signals. The processing device can compute concentration of nucleic acid sequence in each vial.

According to various embodiments, the instrument can include a multi-notch excitation filter between the light source and the beam splitter. The instrument can include a multi-notch emission filter between the beam splitter and the detector. The splitter and filters can be associated with a selected primary dye in the suspension. In another embodiment, a filter module can contain the splitter and filters. The module can be removable from the housing for replacement with another module associated with another selected primary dye. The excitation filter can be a multi-notch filter. The emission filter can be a multi-notch filter. The beam splitter can be a multi-notch beam splitter.

BRIEF DESCRIPTION OF THE DRAWINGS

Various embodiments of the present teachings are exemplified in the accompanying drawings. The teachings are not limited to the embodiments depicted, and include equivalent structures and methods as set forth in the following description and known to those of ordinary skill in the art. In the drawings.

Figure 1:
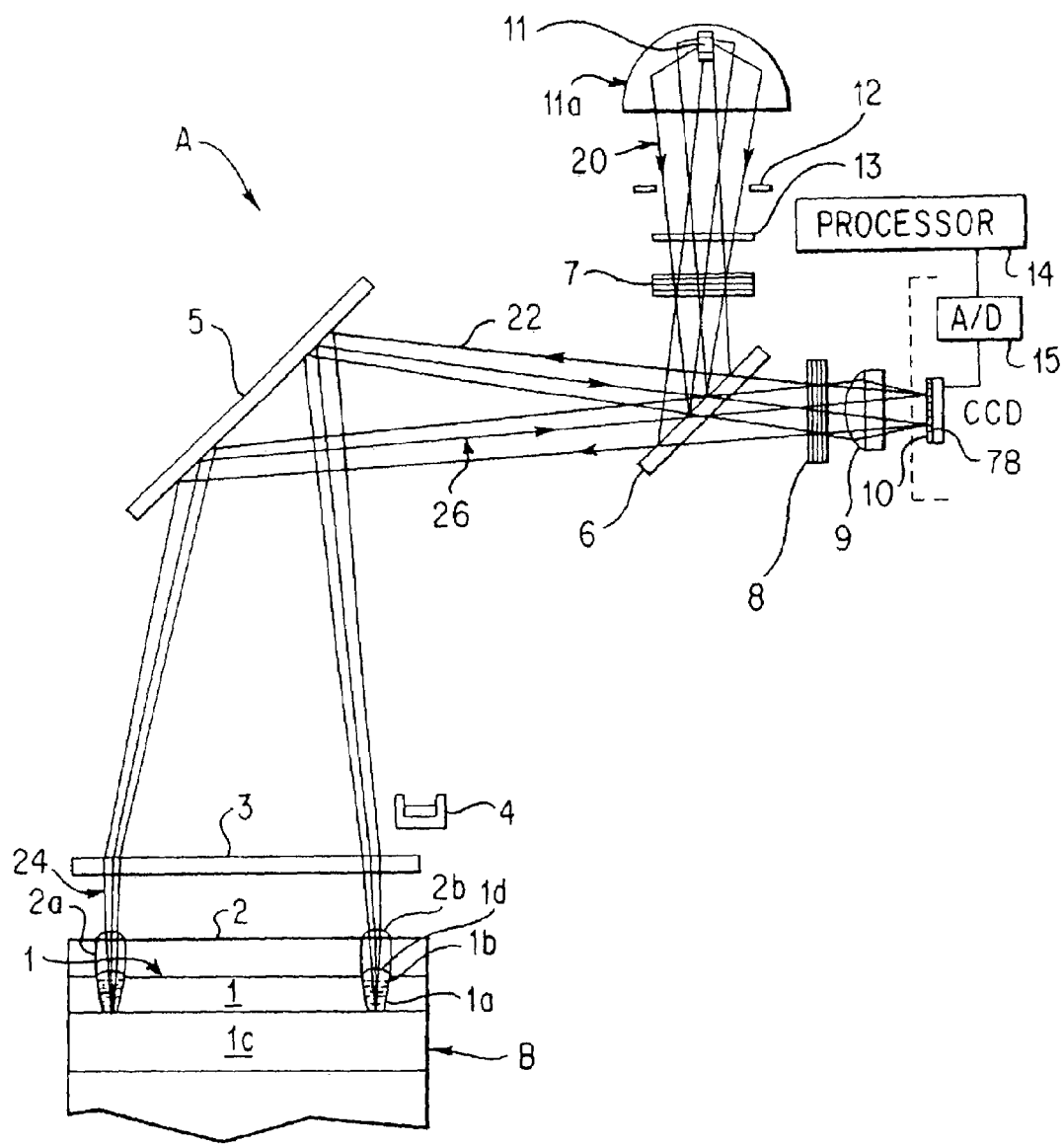
FIG. 1 is a schematic of an optical train for an optical instrument according to various embodiments, associated with a nucleic acid sequence amplification reaction apparatus.

It is to be understood that both the foregoing general description and the following detailed description are exemplary and explanatory only and are intended to provide a further explanation of the various embodiments of the present teachings.

DESCRIPTION

According to various embodiments, a instrument is provided that includes an excitation light source, at least one reaction region capable of retaining at least one respective sample that is capable of emitting emission beams along an emission beam path, a multi-notch filter disposed along an excitation beam path between the excitation light source and the at least one reaction region, and a detector arranged along the emission beam path. The at least one reaction region can include a plurality of reaction regions, for example, 96 reaction wells. The instrument can further include a second multi-notch filter disposed along an emission beam path between the at least one reaction region and the detector.

According to various embodiments, an instrument is provided that includes an excitation light source, at least one reaction well capable of retaining at least one respective sample that is capable of emitting emission beams along an emission beam path, a detector disposed along the emission beam path and capable of detecting emission beams emitted from the at least one reaction well, and a multi-notch filter spaced along the emission beam path between the at least one reaction well and the detector.

According to various embodiments, detectable emission beams can be generated by a number of compounds, including many dyes. According to various embodiments, an optical instrument can be provided that includes a light source arranged to emit an excitation wavelength or wavelength range toward a region capable of retaining a sample, such that a fluorescent dye, if present in the region, can be caused to fluoresce. The light source can provide excitation wavelength ranges that correspond to respective excitation wavelength ranges of a plurality of fluorescent dyes. A detector capable of detecting an emission wavelength emitted from a fluorescing dye can be used to determine the absence or presence of a component associated with the dye. For example, the dyes can include intercalating dyes, reporter dyes, free-floating dyes, and the like.

According to various embodiments, PCR dyes can be used that only fluoresce when bound to a target molecule. Nucleic acid sequence amplification dyes can also be attached to probes that also are connected to quenchers, and the action of nucleic acid sequence amplification enzymes will disassemble the dye-probe-quencher molecule causing the dye to increase its fluorescence. According to various embodiments, nucleic acid sequence amplification can be performed using a variety of methods, for example, polymerase chain reaction (PCR), isothermal amplification reaction, well known in the art. When a PCR procedure is used, for example, the number of unquenched dye molecules doubles with every thermal cycle. Fluorescing dyes are well known in the art, and any of a plurality of fluorescent dyes having various excitation wavelengths can be used. Examples of such dyes include, but are not limited to, Rhodamine, Fluoroscein, dye derivatives of Rhodamine, dye derivatives of Fluoroscein, 5-FAM™, 6-carboxyfluorescein (6-FAM™), VIC™, hexachloro-fluorescein (HEX™), tetrachloro-fluorescein (TET™), ROX™, and TAMRA™. Dyes or other identifiers that can be used include, but are not limited to, fluorophores and phosphorescent dyes. Dyes can be used in combinations of two, three, four, or more dyes per sample. According to various embodiments, the family of 5-FAM™, 6-FAM™, VIC™, TET™, and/or ROX™ dyes can be used to indicate the presence of sample components.

According to various embodiments, various detectable markers can be used, in addition or in alternate, to dyes. Markers can include, for example, fluorescing dyes, free-floating dyes, reporter dyes, probe dyes, intercalating dyes, and molecular beacons. Dyes that fluoresce when integrated into DNA can be intercalating dyes. Other dyes known as "reporter" dyes can attached to the ends of "probes" that have "quenchers" on the other end. A nucleic acid sequence amplification reaction, for example, PCR, can result in the disassembly of the Dye-Probe-Quencher molecule, so the reporter dye can emit an increased amount of fluorescence. Reporter dyes are not attached in any way to the sample. Free floating dyes can be floating freely in solution. Other fluorescing markers well know in the art can be utilized. According to various embodiments, molecular beacons can be single-stranded molecules with hairpins that preferentially hybridize with an amplified target to unfold. According to various embodiments, quantum dots can be used as markers also.

According to various embodiments, a method is provided that includes the detection of a reference. For a reference, a fluorescent reference compound can be caused to emit reference light in response to being exposed to excitation beams. The reference can be disposed to be receptive of a portion of the excitation beams from the excitation source. A portion of the reference light can be passed by a second device as a reference beam to the detector. The reference light can be used to generate reference signals for utilization in the computing of the concentration of DNA. In another embodiment, the reference member can include a plurality of reference emitters. Each reference emitter can emit reference beams of different intensity in response to the excitation beams. The processing device, for example, can then select a reference set including the highest data signals that can be less than a predetermined maximum that can be less than the saturation limit. A multi-notch filter can be used with reference emitters to filter the reference beams.

According to various embodiments, the detector can be operatively connected to the processing device. The detector can integrate emission beam input over a pre-selected exposure time for generating each set of data signals. The processing device, the detector, or a combination thereof can include a saturation limit for the data signals. In another embodiment, the processing device can include an adjustment device for automatically effecting adjustments in exposure time to maintain the primary data within a predetermined operating range for maintaining corresponding data signals less than the saturation limit. The processing device, for example, can include a device for correcting the primary data in proportion to the adjustments in exposure time.

According to various embodiments, the processor can compute photoreceptor data from the data signals for each photoreceptor. The adjustment device can ascertain highest photoreceptor data. The adjustment device can determine whether the highest photoreceptor data can be less than, within or higher than the predetermined operating range. Based on such determination, the exposure time can be increased, retained or reduced so as to effect a subsequent exposure time for maintaining subsequent photoreceptor data within the predetermined operating range. The processing device can detect and/or discern excitation, reference, and/or emission beams, any of which can be first passed through a multi-notch filter.

According to various embodiments, the terms "polynucleotide," "nucleic acids," "nucleotide," "DNA," and "RNA," as used herein, are used interchangeably and can include nucleic acid analogs that can be used in addition to or instead of nucleic acids. Examples of nucleic acid analogs includes the family of peptide nucleic acids (PNA), wherein the sugar/phosphate backbone of DNA or RNA has been replaced with acyclic, achiral, and neutral polyamide linkages. For example, a probe or primer can have a PNA polymer instead of a DNA polymer. The 2-aminoethylglycine polyamide linkage with nucleobases attached to the linkage through an amide bond has been well-studied as an embodiment of PNA and shown to possess exceptional hybridization specificity and affinity. An example of a PNA is as shown below in a partial structure with a carboxyl-terminal amide:

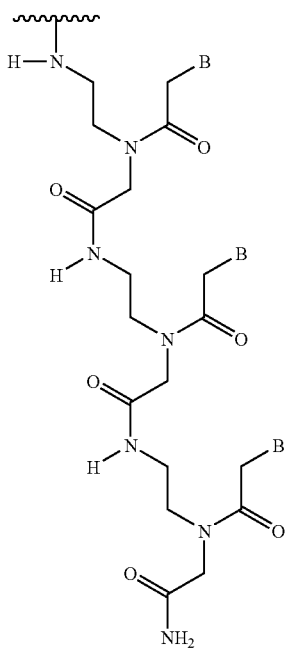

"Nucleobase" as used herein means any nitrogen-containing heterocyclic moiety capable of forming Watson-Crick hydrogen bonds in pairing with a complementary nucleobase or nucleobase analog, e.g. a purine, a 7-deazapurine, or a pyrimidine. Typical nucleobases are the naturally occurring nucleobases such as, for example, adenine, guanine, cytosine, uracil, thymine, and analogs of the naturally occurring nucleobases, e.g. 7-deazaadenine, 7-deazaguanine, 7-deaza-8-azaguanine, 7-deaza-8-azaadenine, inosine, nebularine, nitropyrrole, nitroindole, 2-aminopurine, 2-amino-6-chloropurine, 2,6-diaminopurine, hypoxanthine, pseudouridine, pseudocytosine, pseudoisocytosine, 5-propynylcytosine, isocytosine, isoguanine, 7-deazaguanine, 2-azapurine, 2-thiopyrimidine, 6-thioguanine, 4-thiothymine, 4-thiouracil, $O^6$-methylguanine, $N^6$-methyladenine, $O^4$-methylethymine, 5,6-dihydrothymine, 5,6-dihydrouracil, 4-methylindole, pyrazolo[3,4-D]pyrimidines, "PPG", and ethenoadenine.

"Nucleoside" as used herein refers to a compound consisting of a nucleobase linked to the C-1' carbon of a sugar, such as, for example, ribose, arabinose, xylose, and pyranose, in the natural β or the α anomeric configuration. The sugar can be substituted or unsubstituted. Substituted ribose sugars can include, but are not limited to, those riboses having one or more of the carbon atoms, for example, the 2'-carbon atom, substituted with one or more of the same or different Cl, F, —R, —OR, —$NR_2$ or halogen groups, where each R is independently H, $C_1$-$C_6$ alkyl or $C_5$-$C_{14}$ aryl. Ribose examples can include ribose, 2'-deoxyribose, 2',3'-dideoxyribose, 2'-haloribose, 2'-fluororibose, 2'-chlororibose, and 2'-alkylribose, e.g. 2'-O-methyl, 4'-α-anomeric nucleotides, 1'-α-anomeric nucleotides, 2'-4'- and 3'-4'-linked and other "locked"

or "LNA", bicyclic sugar modifications. Exemplary LNA sugar analogs within a polynucleotide can include the following structures:

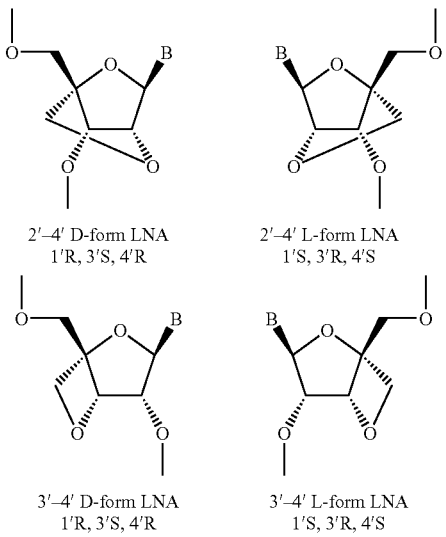

where B is any nucleobase.

Sugars can have modifications at the 2'- or 3'-position such as methoxy, ethoxy, allyloxy, isopropoxy, butoxy, isobutoxy, methoxyethyl, alkoxy, phenoxy, azido, amino, alkylamino, fluoro, chloro and bromo. Nucleosides and nucleotides can have the natural D configurational isomer (D-form) or the L configurational isomer (L-form). When the nucleobase is a purine, e.g. adenine or guanine, the ribose sugar is attached to the $N^9$-position of the nucleobase. When the nucleobase is a pyrimidine, e.g. cytosine, uracil, or thymine, the pentose sugar is attached to the $N^1$-position of the nucleobase.

"Nucleotide" as used herein refers to a phosphate ester of a nucleoside and can be in the form of a monomer unit or within a nucleic acid. "Nucleotide 5'-triphosphate" as used herein refers to a nucleotide with a triphosphate ester group at the 5' position, and can be denoted as "NTP", or "dNTP" and "ddNTP" to particularly point out the structural features of the ribose sugar. The triphosphate ester group can include sulfur substitutions for the various oxygens, e.g. α-thionucleotide 5'-triphosphates.

As used herein, the terms "polynucleotide" and "oligonucleotide" mean single-stranded and double-stranded polymers of, for example, nucleotide monomers, including 2'-deoxyribonucleotides (DNA) and ribonucleotides (RNA) linked by internucleotide phosphodiester bond linkages, e.g. 3'-5' and 2'-5', inverted linkages, e.g. 3'-3' and 5'-5', branched structures, or internucleotide analogs. Polynucleotides can have associated counter ions, such as $H^+$, $NH_4^+$, trialkylammonium, $Mg^{2+}$, $Na^+$ and the like. A polynucleotide can be composed entirely of deoxyribonucleotides, entirely of ribonucleotides, or chimeric mixtures thereof. Polynucleotides can be comprised of internucleotide, nucleobase and sugar analogs. For example, a polynucleotide or oligonucleotide can be a PNA polymer. Polynucleotides can range in size from a few monomeric units, e.g. 5-40 when they are more commonly frequently referred to in the art as oligonucleotides, to several thousands of monomeric nucleotide units. Unless otherwise denoted, whenever a polynucleotide sequence is represented, it will be understood that the nucleotides are in 5' to 3' order from left to right and that "A" denotes deoxyadenosine, "C" denotes deoxycytidine, "G" denotes deoxyguanosine, and "T" denotes thymidine, unless otherwise noted.

"Internucleotide analog" as used herein means a phosphate ester analog or a non-phosphate analog of a polynucleotide. Phosphate ester analogs can include: (i) $C_1$-$C_4$ alkylphosphonate, e.g. methylphosphonate; (ii) phosphoramidate; (iii) $C_1$-$C_6$ alkyl-phosphotriester; (iv) phosphorothioate; and (v) phosphorodithioate. Non-phosphate analogs can include compounds wherein the sugar/phosphate moieties are replaced by an amide linkage, such as a 2-aminoethylglycine unit, commonly referred to as PNA.

According to various embodiments, an optical instrument A can be utilized with or incorporated into a reaction apparatus B that replicates ("amplifies") selected portions of DNA by nucleotide amplification reaction. The nucleotide amplification or replication reaction can be a thermal or isothermal reaction. The nucleotide amplification reaction can be a polymerase chain reaction ("PCR").

According to various embodiments, the reaction can occur in a reaction region, for example, a well. Herein, "well" can mean a recess in a substrate, a container, or a vial, for example. "Well" does not refer to capillary electrophoresis channels in substrates or electrophoresis capillaries.

The reaction apparatus can be conventional and can function without interference from the instrument which can monitor the amount of nucleic acid in real time during replication. Suitable reaction apparatus are described in U.S. Pat. Nos. 5,475,610 and 5,656,493.

In a thermal nucleotide amplification reaction, for example, PCR, the reaction apparatus (FIG. 1) can be conventional and can include two main components, namely a thermal cycler block 1 with wells 1a for holding at least one vial 1b containing a suspension of ingredients for the reaction, and a thermal cycle controller 1c for cycling the temperature of the block through a specified temperature program. The starting ingredients of the aqueous suspension of sample materials can include a "seed" sample of a nucleic acid sequence, selected nucleic acid sequence primer strands, nucleic acid sequence elements, nucleic acid sequence fragments, enzymes, other chemicals, or a combination thereof. The block, for example, aluminum, can be heated and cooled in a prescribed cycle by an electrical device, liquid or air coolant devices, or a combination of these, or other devices to achieve the cycling. The suspensions in the vials can be cycled between two temperature phases so as to effect the thermal nucleotide amplification reaction. These phases can be a lower temperature extension phase for the PCR reaction of about 60° C., which can be the phase where all of the nucleic acid sequence strands have recombined into double strands. A high temperature denaturing phase at about 95° C. can be part of the PCR reaction, during which the nucleic acid sequence can be denatured or split into single strands.

According to various embodiments, a sample can contain a fluorescent dye that fluoresces proportionately and more strongly in the presence of double stranded nucleic acid sequences to which the dye binds, for example SYBR Green dye. The SYBR Green dye is available from Molecular Probes, Inc., Eugene, Oreg. The SYBR Green dye can fluoresce in the presence of double stranded nucleic acid sequences. Another type of fluorescent dye labeled "probes", which can be DNA-like structures with complimentary sequences to selected nucleic acid sequence strand portions, can be used. Other dyes that have similar characteristics can be utilized. As used herein and in the claims, the term "marker dye" refers to the type that binds to double stranded nucleic acid sequences, or to the probe type, or to any other type of dye that attaches to nucleic acid sequences so as to fluoresce in proportion to the quantity of a nucleic acid sequences. Samples can also contain an additional, passive dye (independent of the nucleic acid sequence) to serve as a reference as described below. Under incidence of light including a correct excitation frequency, a dye can fluoresce to emit light at an emission frequency. The emission frequency can be lower than that of the excitation light.

According to various embodiments, the vials can be formed conically. The vials can be formed in a plastic unitary tray. The tray can contain a plurality of vials, for example, 96 vials in an array of 12 by 8. The tray can be removable from the block for preparations. A plastic unitary cover with caps 1d for the vials can rest or attach over the vials to prevent contamination and evaporation loss. Other devices can be used for this function, for example, oil on the sample surface. If other devices are used to cover the tray, the vials caps may not be necessary. The caps can be transparent to light utilized in the instrument, for example, the excitation frequency. The caps can be convex. The caps can face towards the light source or upwardly.

According to various embodiments, the monitoring instrument can be mounted over the block containing the vials. The instrument can be removable or swing away for access to the vials. In the bottom of the instrument, a platen 2 can rest over the vial caps or, if none, directly over the vials. The platen can be metal, for example, aluminum. The platen can include an array of holes 2a therethrough aligned with the vials. Each hole can have a diameter about the same as the vial top diameter. The platen can have its temperature maintained by a film heater or other devices for heating the platen. When caps are used, the heating can be controlled to prevent condensation under the caps without interfering with nucleic acid sequence replication in the vials, for example, by holding the platen at a slightly higher temperature than the highest sample temperature that the thermal cycler reaches.

As depicted in FIG. 1, above each of the vials, a lens 2b can be positioned such that its focal point is approximately centered above the suspension in the vial. Above these lenses, a field lens 3 can be provided as a telecentric optical system. According to various embodiments, the field lens 3 can be an aspherically corrected Fresnel lens for minimal distortion. A neutral density pattern (not shown), to correct nonuniformities in illumination and imaging, can be mounted on or in proximity to the field lens, for example, to attenuate light in the center of the image field. A folding optical mirror can be optionally mounted, for example, at 45°, for convenient packaging. The folding optical mirror can be omitted, or other folding optics well known in the art, can be used. According to various embodiments, the field lens and/or the vial lenses, can each include two or more lenses that effect the required focusing. The word "lens" herein can include such multiplicities of lenses.

According to various embodiments, a light source 11 for a source beam 20 of light can be provided. The light source can provide a flood light, for example, a 100 watt halogen lamp. The light source can provide light at selective wavelengths, incoherent or incoherent. According to various embodiments, the light source can be mounted at a focal distance of an ellipsoid reflector 11a which can produce a relatively uniform pattern over the desired area. According to various embodiments, the reflector can be dichroic. The dichroic reflector can, for example, substantially reflect visible light and transmit infrared light, to restrict infrared from the other optical components, and from overheating the instrument. The cooling of the instrument can be aided by a heat reflecting mirror 13 in the optical path. A mechanical or electronic shutter 12 can be used for blocking the source beam of the light source for obtaining dark data. The type of light source can be a projection lamp, or a laser, with appropriate optical elements.

According to various embodiments, a beam splitter 6 can be disposed to receive the source beam 20. In the present embodiment this can be a dichroic reflector positioned, for example, at 45°, to reflect light including an excitation frequency that can cause the marker dye to fluoresce at an emission frequency. The dichroic reflector can pass light including the emission frequency. Such a conventional optical device can utilize optical interference layers to provide the specific frequency response.

According to various embodiments, the beam splitter can be positioned to reflect the source beam to the folding mirror. The source beam can be reflected from the splitter as an excitation beam 22 including substantially the excitation frequency. The excitation beam can be focused by the field lens 3 and then as separated beams 24 by the vial (well) lenses 2b into the center of the vials. The marker dye can be thereby caused to emit light at the emission frequency. This light can be passed upwardly, as depicted in FIG. 1, as an emission beam in the form of individual beams 26. The individual beams 26 can be reflected from the folding mirror 5 to the beam splitter 6, which can pass the emission beam through to a detector 10.

According to various embodiments, the vial lenses 2b and the field lens 3 can together constitute a primary focusing device for focusing both the excitation beam and the emission beam. According to various embodiments, the field lens can be omitted from the focusing device. According to various embodiments, the vial lenses can be omitted from the focusing device. In another embodiment, an objective lens in the field lens position can be used to focus the individual emission beams on the detector.

According to various embodiments, the beam splitter 6 can pass the source beam as an excitation beam and reflect the emission beam, with appropriate rearrangement of the lamp and the detector. Angles other than 45° can be used depending on the beam splitter utilized. The beam splitter can be used to form a more perpendicular reflection and pass through. The beam splitter can split the optical paths for the excitation beam and the emission beam. Other variations known in the art that achieve this can also be suitable. The dichroic device can help minimize the source light reaching the detector. A can also be used. The non-dichroic beam splitter can be less efficient as significant amounts of source light are reflected or transmitted in the wrong direction, for example, to the detector, and/or lost.

According to various embodiments, to further filter the source light, an excitation filter 7 can be disposed between the light source 11 and the beam splitter 6. This can pass light including the excitation frequency while substantially blocking light including the emission frequency. Similarly, an emission filter 8 can be disposed between the beam splitter and the detector, in this case between the splitter and a detector lens 9 in front of the detector. This filter can pass light including the emission frequency while substantially blocking light including the excitation frequency.

According to various embodiments, a lens can be used as a detector lens to focus the emission frequency. A focusing reflector can be used for the detector lens. Such an emission focusing device, detector lens, or reflector, can be located after, as shown, or before the beam splitter. The emission focusing device can be on either side of the emission filter. The emission focusing device can be integrated into the primary focusing device. The field lens can be an objective lens, for example, that focuses the emission beam onto the detector.

According to various embodiments, suitable filters can be conventional optical bandpass filters utilizing optical interference films, each having a bandpass at a frequency optimum either for excitation of the fluorescent dye or its emission. Each filter can have very high attenuation for the other (non-bandpass) frequency, in order to prevent "ghost" images from reflected and stray light. For SYBR Green dye, for example, the excitation filter bandpass wavelength can center around 485 nm, and the emission filter bandpass wavelength can center around 555 nm. The beam splitter can transition from reflection to transmission between these two, e.g. about 510 nm, so that light less than this wavelength can be reflected and higher wavelength light can be passed through.

According to various embodiments, a light source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, or combinations thereof.

According to various embodiments, one or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light sources and a sample. One or more emission filters can be associated with an emission beam from an excited dye. One or more filters can be located between the sample and one or more emission beam detectors.

According to various embodiments, a filter can be a single bandpass filter or a multiple bandpass filter. As used herein, a bandpass filter and a passband filter can be used interchangeably. A multiple passband filter can be, for example, a multi-notch filter, a multi-Rugate filter, or simply a Rugate filter. A multiple passband filter can be used with an incoherent light source, for example, a halogen lamp, a white light source, and/or one or more Light Emitting Diode (LED), or Organic LEDs emitting light at different wavelengths. A multiple passband filter can be used with a multiple laser-based light source emitting light at different wavelengths. Examples of manufacturing Rugate filters and Rugate beam splitters can be found in, for example, U.S. Pat. No. 6,256,148 to Gasworth, which is incorporated herein by reference in its entirety.

According to various embodiments, a multiple passband filter can be used with a dichroic beam splitter, a 50/50 beam splitter, a dichroic beam splitter that has several "passbands," or no beam splitter. A multiple beam splitter can be coated at an angle, causing a variance in a thickness across a filter substrate, to compensate for wavelength shift with an angle. A multiple passband filter can be formed by coating different light interference materials over respective areas of a substrate used in a multiple passband filter manufacture.

According to various embodiments, a Rugate filter can be an example of an interference coating based on the refractive index that varies continuously in a direction, for example, perpendicular or 45 degrees to the film plane. When the refractive index varies periodically within two extreme values, a minus filter with high transmittance on either side of the rejection band can be made. Periodic Rugate filters can be manufactured. In principle, a Rugate filter can be an interference coating based on a refractive index that varies continuously (not in discrete steps) in the direction perpendicular to the film plane. When the refractive index varies periodically and within two extreme values, it can be possible to design a rejection filter with high reflectance, approaching 99%, in the middle, and high transmission, approaching 99%, on either side of the rejection band. The Rugate filter can be designed to eliminate side-lobes, higher harmonics, and other significant parasitic losses. A Rugate filter overlay can have conjugate reflectance/transmittance characteristics matching the desired spectral response.

According to various embodiments, Rugate notch filters can use refractory metal oxides to achieve coatings with exceptional thermal and environmental stability. These filters can be used in place of other types of notch filters, particularly where durability and reliability are desired. Rugate notch filters are available from Barr Associates (Westford, Mass.). The Rugate notch filter can be used as edge filters and beam splitters. Filter sizes or shapes are generally not limitations for the Rugate notch filter. The Rugate notch filter can provide environmental and thermal stability, a broad operating temperature range, narrow rejection bands, variety of shapes & sizes, high throughput, low ripple, and/or a broad spectral range. More information is available from, for example, www.barr-associates-uk.com, www.barrassociates.com/opticalfilters.php.

According to various embodiments, multi-notch filters can be made, for example, with a measured blocking of O.D. 6 or better. Notch filters with this type of deep blocking level at the light wavelength can also afford high transmission close to the light line.

According to various embodiments, excitation levels can increase when multiple dyes spaced apart spectrally are irradiated with excitation beams. This can lead to less spectral crosstalk. The dye matrix, condition number, and/or deconvolution in a system can be improved. The increased excitation levels can provide higher signal levels. Higher signal levels can be seen during the utilization of dyes that emit in the "red" spectrum. The dynamic range of the system can be improved. The system can reduce the compensation for variation in the emission beam intensity for various dyes.

More broadly, the excitation filter and the beam splitter can together constitute a first device disposed to be receptive of the source beam to effect an excitation beam including the excitation frequency, and the emission filter and the beam splitter together constitute a second device disposed to be receptive of the emission beam from the focusing device so as to pass the emission beam at the emission frequency to the detector. Also, as mentioned above, the beam splitter alternatively can pass the source beam as an excitation beam and reflect the emission beam to the detector. In another aspect, the filters can be omitted, and the first device can be represented by the beam splitter effecting the excitation beam from the source beam, and the second device can be represented by the beam splitter passing the emission beam to the detector.

According to various embodiments, the beam splitter can be omitted, and the first device can constitute an excitation frequency, the second device can constitute an emission filter for the emission frequency, where the light source and the detector can be side by side so that the excitation and emission beams can be on slightly different optical paths angularly. The source and detector need not actually be side by side with one or more folding mirrors. Thus any such arrangement for achieving the effects described herein can be deemed equivalent. According to various embodiments, the beam splitter can be capable of passing the excitation and emission beams through the field lens, allowing the excitation and emission beams to have a common optical path, fully or partially.

According to various embodiments, the beam splitter 5 in FIG. 1 can be replaced with a 50/50 beam splitter, or a dichroic that has several passbands. A multi-notch filter, or a Rugate filter can be used as dichroic that has several passbands.

According to various embodiments, the light source can be a Light Emitting Diode (LED). The LED can be, for example, an Organic Light Emitting Diode (OLED), a Thin Film Electroluminescent Device (TFELD), or a Quantum dot based inorganic "organic LED." The LED can include a phosphorescent OLED (PHOLED). As used herein, the terms "excitation source" and "light source" are used interchangeably.

According to various embodiments, excitation beams emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as a focusing lens.

According to various embodiments, a light source can contain one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments wherein the LED or array of LEDs can emit, for example, at least about 50 mW of excitation energy, a cooling device such as, but not limited to, a heat sink or fan can be used with the LED. An array of high-powered LEDs can be used that draws, for example, about 10 watts of energy or less, about 10 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Exemplary LED array sources are available, for example, from Stocker Yale under the trade name LED AREALIGHTS. According to various embodiments, LED light sources can use about 1 microwatt of power or less, for example, about 1mW, about 5 mW, about 25 mW, about 50 mW, about 1W, about 5W, about 50W, or about 100W or more, individually or when in used in an array.

According to various embodiments, a quantum dot can be used as a source for luminescence and as a fluorescent marker. The quantum dot based LED can be tuned to emit light in a tighter emission bandpass, thus the quantum dot based LED can increase the efficiency of the fluorescent system. Quantum dots can be molecular-scale optical beacons. The quantum dot nanocrystals can behave like molecular LEDs (light emitting diodes) by "lighting up" biological binding events with a broad palette of applied colors. Quantum dots can provide many more colors than conventional fluorophores. Quantum dots can possess many other very desirable optical properties. Nanocrystal quantum dots can be covalently linked to biomolecules using standard conjugation chemistry. The quantum dot conjugate can then be used to detect a binding partner in a wide range of assays. According to various embodiments, streptavidin can be attached to quantum dots to detect biotinylated molecules in a variety of assays. Quantum dots can also be attached to antibodies and oligonucleotides. Any assay that currently uses, for example, fluorescent-tagged molecules, colorimetric enzymes, or colloidal gold, can be improved with quantum dot nanocrystal-tagged conjugates. An exemplary quantum dot implementation is available from Quantum Dot Corporation of Haywood, Calif. under the trademark QDOT. More information about quantum dots and their applications can be found at, for example, www.qdot.com. U.S. Pat. Nos. 6,207,229, 6,251,303, 6,306,310, 6,319,426, 6,322,901, 6,326,144, 6,426,513, and 6,444,143 to Bawendi et al., U.S. Pat. Nos. 5,990,479, 6,207,392, and 6,423,551 to Weiss et al., U.S. Pat. No. 6,468,808 to Nie et al., and U.S. Pat. No. 6,274,323 to Bruchez et al., describe a variety of biological applications, methods of quantum dot manufacturing, and apparatuses for quantum dot nanocrystals and conjugates, all of which are incorporated herein by reference in their entireties.

Quantum dots can provide a versatile probe that can be used in, for example, in multiplex assays. Fluorescent techniques using quantum dot nanocrystals can be much faster than conventional enzymatic and chemiluminescent techniques, can reduce instrument tie-up, and can improve assay throughput. Colorimetric or detected reflectance techniques can be inferior to fluorescence and difficulties can ensue when multiplex assays are developed based on these materials. Quantum dots can absorb all wavelengths "bluer" (i.e., shorter) than the emission wavelength. This capability can simplify the instrumentation required for multiplexed assays, since all different label colors can be excited with a single excitation source.

A Quantum dot based LED can emit light in an emission band that is narrower than an emission band of a normal LED, for example, about 50% narrower or about 25% narrower. The Quantum dot based LED can also emit light at an electrical energy conversion efficiency of about, 90% or more, for example, approaching 100%. OLED films, including Quantum dot based LEDs, can be applied to a thermal block, used for heating and cooling samples, in a fluorescence system without interfering with the operation of the thermal block.

According to various embodiments, when an OLED is used, the OLED can have any of a variety of sizes, shapes, wavelengths, or combinations thereof. The OLED can provide luminescence over a large area, for example, to luminescence multiple sample wells. Scatter or cross-talk light between multiple sample wells for this single OLED can be reduced by either overlaying a mask on the OLED or by patterning the luminescent in the OLED to operatively align with the multiple sample wells. The OLED can be a low power consumption device. Examples of OLEDs in various configurations and wavelengths are described in, for example, U.S. Pat. No. 6,331,438 B1, which is incorporated herein by reference in its entirety. The OLED can include a small-molecule OLED and/or a polymer-based OLED also known as a Light-Emitting Polymer (LEP). A small-molecule OLED that is deposited on a substrate can be used. An OLED that is deposited on a surface by vapor-deposition technique can be used. An OLED can be deposited on a surface by, for example, silk-screening. An LEP can be used that is deposited by, for example, solvent coating.

According to various embodiments, an OLED is used and can be formed from one or more stable, organic materials. The OLED can include one or more carbon-based thin films and the OLED can be capable of emitting light of various colors when a voltage is applied across the one or more carbon-based thin films.

According to various embodiments, the OLED can include a film that is located between two electrodes. The electrodes can be, for example, a transparent anode, a metallic cathode, or combinations thereof. Several separate emission areas can be stimulated between a single set of electrodes where simultaneous illumination of the separate emission areas is required. According to such embodiments, only one power and control module could be required for several apparent light sources. The OLED film can include one or more of a hole-injection layer, a hole-transport layer, an emissive layer, and an electron-transport layer. The OLED can include a film that is about one micrometer in thickness, or less. When an appropriate voltage is applied to the film, the injected positive and negative charges can recombine in the emissive layer to produce light by means of electroluminescence. The amount of light emitted by the OLED can be related to the voltage applied through the electrodes to the thin film of the OLED. Various materials suitable for fabrication of OLEDs are available, for example, from H. W. Sands Corp. of Jupiter, Fla. Various types of OLEDs are described, for example, in U.S. Pat. No. 4,356,429 to Tang, U.S. Pat. No. 5,554,450 to Shi et al., and U.S. Pat. No. 5,593,788 to Shi et al., all of which are incorporated herein by reference in their entireties.

According to various embodiments, an OLED can be used and produced on a flexible substrate, on an optically clear substrate, on a substrate of an unusual shape, or on a combination thereof. Multiple OLEDs can be combined on a substrate, wherein the multiple OLEDs can emit light at different wavelengths. Multiple OLEDs on a single substrate or multiple adjacent substrates can form an interlaced or a non-interlaced pattern of light of various wavelengths. The pattern can correspond to, for example, a sample reservoir arrangement. One or more OLEDs can form a shape surrounding, for example, a sample reservoir, a series of sample reservoirs, an array of a plurality of sample reservoirs, or a sample flow path. The sample path can be, for example, a channel, a capillary, or a micro-capillary. One or more OLEDs can be formed to follow the sample flow path. One or more OLEDs can be formed in the shape of a substrate or a portion of a substrate. For example, the OLED can be curved, circular, oval, rectangular, square, triangular, annular, or any other geometrically regular shape. The OLED can be formed as an irregular geometric shape. The OLED can illuminate one or more sample reservoirs, for example, an OLED can illuminate one, two, three, four, or more sample reservoirs simultaneously, or in sequence. The OLED can be designed, for example, to illuminate all the wells of a corresponding multi-well array.

According to various embodiments, one or more excitation filters can be incorporated into the OLED substrate, thus eliminating additional equipment and reducing the amount of space needed for an optical system. For example, one or more filters can be formed in a layer of a substrate including one or more OLEDs and a layer including a sample flow path. The wavelength emitted by the OLED can be tuned by printing a fluorescent dye in the OLED substrate, as taught, for example, by Hebner et al. in "Local Tuning of Organic Light-Emitting Diode Color by Dye Droplet Application," APPLIED PHYSICS LETTERS, Vol. 73, No. 13 (Sep. 28, 1998), which is incorporated herein by reference in its entirety. When using multiple emission lines in an OLED, the OLED can be used in combination with a multiple notch emission filter.

According to various embodiments, an OLED can be substituted in place of any of the systems, devices, or apparatuses where an LED is shown. The OLED light source can have several OLED films stacked and operatively disposed such that several wavelengths of excitation beams can traverse the same optical path to illuminate the sample well. Several OLEDs forming excitation beams of the same wavelength can be stacked to provide higher output to illuminate the sample well.

According to various embodiments, a sample well can be placed in between an excitation source and a detector. The sample well can be a micro card, for example, a microtiter card, such as a 96-well microtiter card. The excitation source can be, for example, an OLED, standard LED, or combination thereof.

According to various embodiments, the light source can be a Solid State Laser (SSL) or a micro-wire laser. The SSL can produce monochromatic, coherent, directional light and can provide a narrow wavelength of excitation energy. The SSL can use a lasing material that is distributed in a solid matrix, in contrast to other lasers that use a gas, dye, or semiconductor for the lasing source material. Examples of solid state lasing materials and corresponding emission wavelengths can include, for example: Ruby at about 694 nm; Nd:Yag at about 1064 nm; Nd:YVO4 at about 1064 nm and/or about 1340 nm and which can be doubled to emit at about 532 nm or about 670 nm; Alexandrite at from about 655 nm to about 815 nm; and Ti:Sapphire at from about 840 nm to about 1100 nm. Micro-wire lasers are lasers where the wavelength of an excitation beam formed by the laser can be tuned or adjusted by altering the size of a wire. According to various embodiments, other solid state lasers known to those skilled in the art can also be used, for example, laser diodes. The appropriate lasing material can be selected based on the fluorescing dyes used, the excitation wavelength required, or both.

According to various embodiments, if a SSL is used, the laser can be selected to closely match the excitation wavelength of a fluorescent dye. The operating temperature of the system can be considered in selecting an appropriate SSL. The operating temperature can be regulated or controlled to change the emitted wavelength of the SSL. The light source for the laser can be any source as known to those skilled in the art, such as, for example, a flash lamp. Useful information about various solid state lasers can be found at, for example, www.repairfaq.org/sam/lasersl.htm. Examples of solid state lasers used in various systems for identification of biological materials can be found in, for example, U.S. Pat. No. 5,863,502 to Southgate et al. and U.S. Pat. No. 6,529,275 B2 to Amirkhanian et al.; both of which are incorporated herein by reference in their entireties.

According to various embodiments, various types of light sources can be used singularly or in combination with other light sources. One or more OLEDs can be used with, for example, one or more non-organic LEDs, one or more solid state lasers, one or more halogen light sources, or combinations thereof.

Figure 1A:
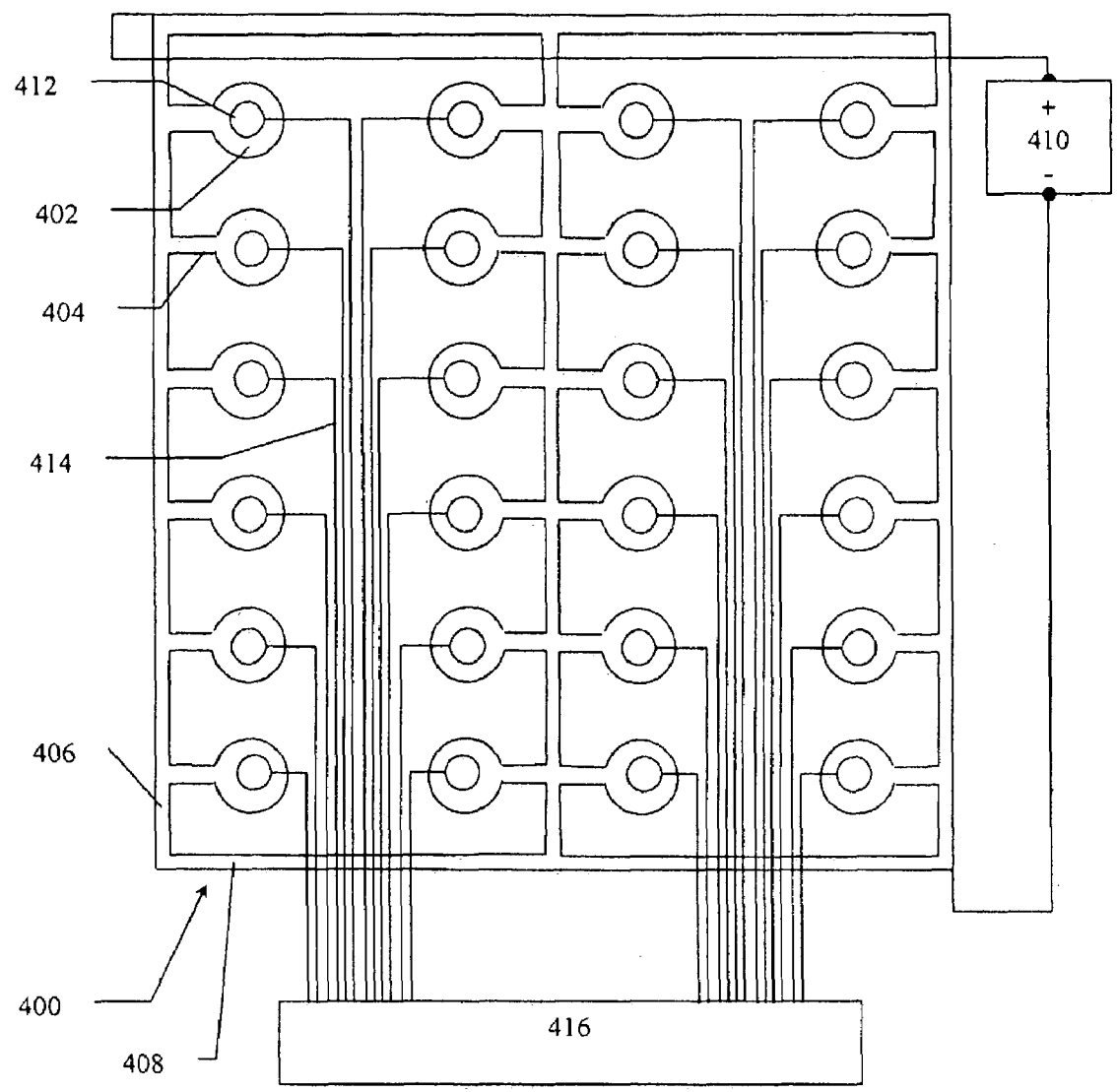
FIG. 1a illustrates an exemplary embodiment of a light source layout, for example, an organic light emitting diode (OLED) layout.

FIG. 1a is a bottom view that illustrates an OLED layout 400 that can be used as a light source, together with a plurality of photodiode detectors 412, according to various embodiments. The OLED layout 400 can include a plurality of OLED well lamps 402, each positioned, when in operation, above a respective well of a multi-well sample well array. Each OLED material well lamp 402 can be connected to, or integrally formed with, a respective connection arm 404 that leads to a layout terminal 406. Each layout terminal can be connected to or integrally formed with the respective connection arms 404 branching from the layout terminal.

According to various embodiments, the connection arms 404 can branch off of side terminals 406 and 408. The OLED layout can be connected to respective opposite electrical connections, for example, opposite terminals of a power supply. The OLED layout can be connected to the power supply through leads arranged at opposite corners of the OLED layout. The power supply can include or be connected to one or more of a switch, a meter, an oscillator, a potentiometer, a detector, a signal processing unit, or the like. Alternatively, or additionally, connection arms 404 can each include a wire or electrical lead in the form of, for example, a metal wire. The OLED layout can include a plurality of individually addressable OLED lighting elements (not shown) with a separate lead connected to each lighting element. The wiring, leads, terminals, connection arms, and the like can be implemented in, for example, a substrate or a film. An OLED layout control unit 410 can be used to supply power and control the OLED layout 400. A plurality of detectors 412 can be electrically connected to a detector control unit 416 through respective detector leads 414 as shown.

According to various embodiments, the plurality of detectors can be arranged, for example, centered, on the plurality of OLED well lamps 402, on the sides of well lamps that face respective sample wells, and/or when operatively positioned adjacent a multi-well sample well array. The detectors can be configured to detect light emitted from the sample wells of a sample well array, without being flooded or bleached out by the respective OLED well lamps. For example, a mask material can be disposed between the detectors and the respective OLED well lamps. The detector 412 can be formed in the same substrate as the OLED lamp.

According to various embodiments, the exemplary OLED layout shown in FIG. 1a is shaped to be aligned with a 24 well sample well array. Other embodiments of OLED layouts using various shapes and various numbers of well lamps are within the scope of the present teachings.

According to various embodiments, each well lamp 402 can include, for example, four individual lamps or OLED layers, capable of producing excitation wavelengths at four different frequencies.

According to various embodiments, the OLED layout can be constructed of a unitary or multi-part construction, of molded material, of stamped material, of screen printed material, of cut material, or the like.

Figure 1B:
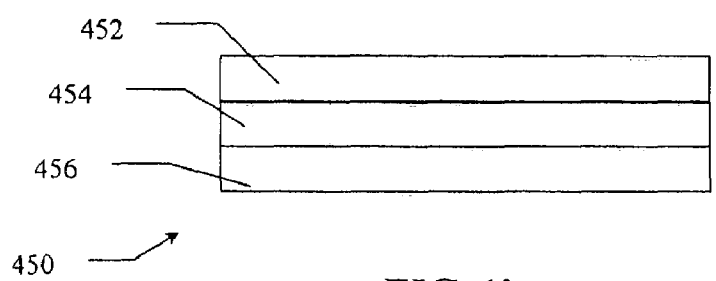
FIG. 1b illustrates an exemplary embodiment of a light source layout, for example, an OLED layout with varying color OLEDs stacked upon each other.

FIG. 1b illustrates an exemplary embodiment of a light source layout. An OLED layout 450 can include varying color OLEDs 452, 454, and 456 stacked upon each other. The layout can be useful for a compact light source design capable of forming excitation beams at varying wavelengths. The OLEDs 452, 454, and 456 can be transparent, allowing excitation beams from each OLED to pass through any other OLED so as to be directed towards a sample. The OLEDs 452, 454, and 456 can emit different colors, same colors, or a combination thereof depending on the color intensity and variety required. The OLEDs 452, 454, and 456 can share an electrode, for example, a cathode. One electrode, for example, an anode, for powering each of the OLEDs 452, 454, and 456 can be connected in electrical isolation from each respective anode to a control unit (not shown) if the capability to independently activate each of the OLEDs 452, 454, and 456 is desired. The OLEDs 452, 454, and 456 can electrically share one electrode, two electrodes, or no electrodes. Any number of OLEDs can be stacked, for example, two OLEDs, three OLEDs, four OLEDs, or more OLEDs, to form a light source, a respective light source, or an array of light sources.

According to various embodiments, multiple excitation wavelengths can be used to detect multiple sample components. According to various embodiments, the apparatus and method can be adapted for use by any suitable fluorescence detection system. For example, various embodiments of the apparatus and method can be used in a sequencing system with single or multiple samples, for example, in a nucleic acid sequence amplification reaction, in a sequencing detection system.

Figure 2:
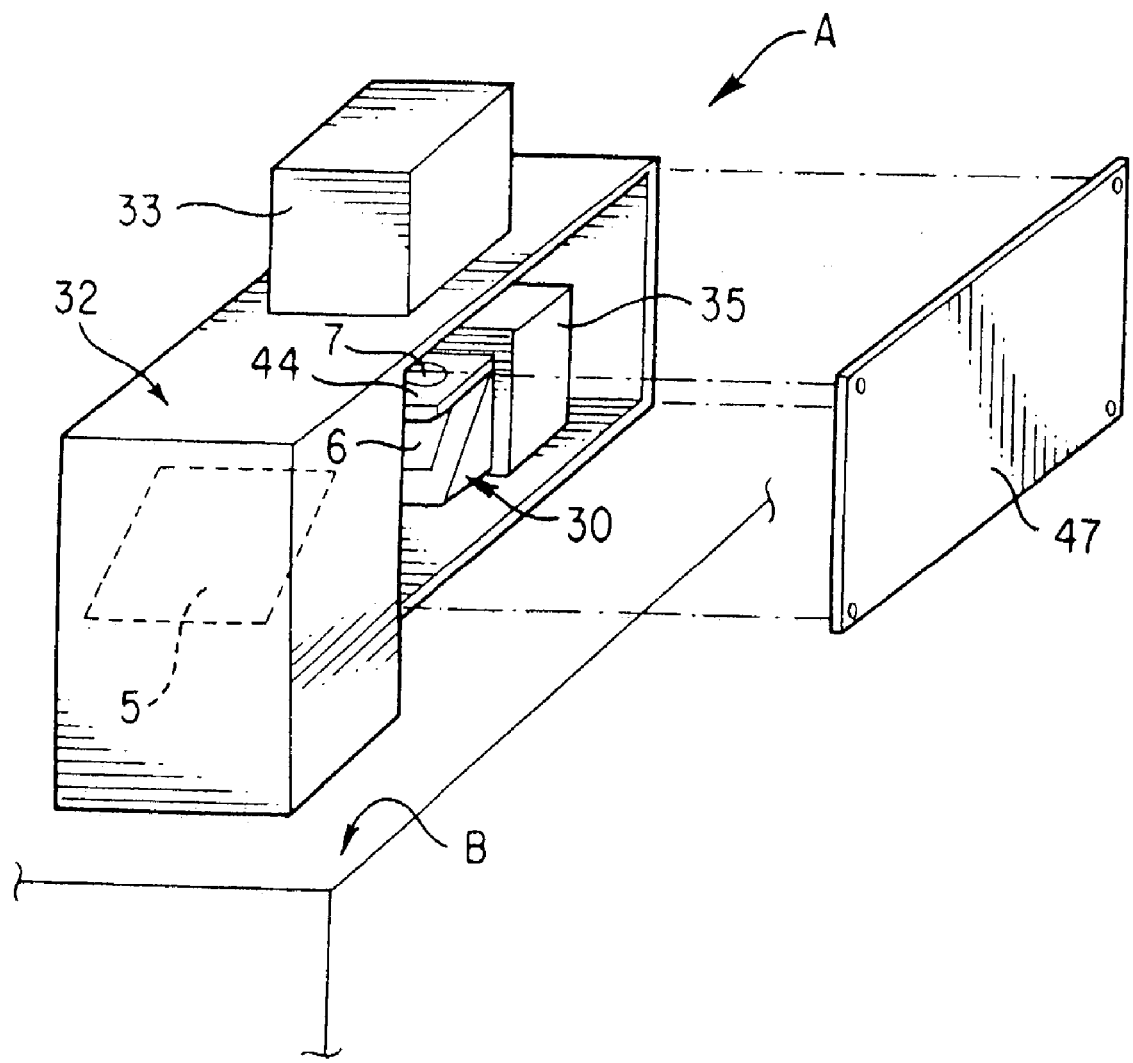
FIG. 2 is a perspective of the instrument of FIG. 1 with a side panel removed.

According to various embodiments, the beam splitter 6, the excitation filter 7 and the emission filter 8 can be affixed in a module 30 (FIG. 2) that can be associated with a selected primary dye for the suspension. The module can be removable from the housing 32 of the instrument A for replacement with another module containing different beam splitter and filters associated with another selected primary dye. The instrument can include a lamp subhousing 33 and a camera subhousing 35.

Figure 3:
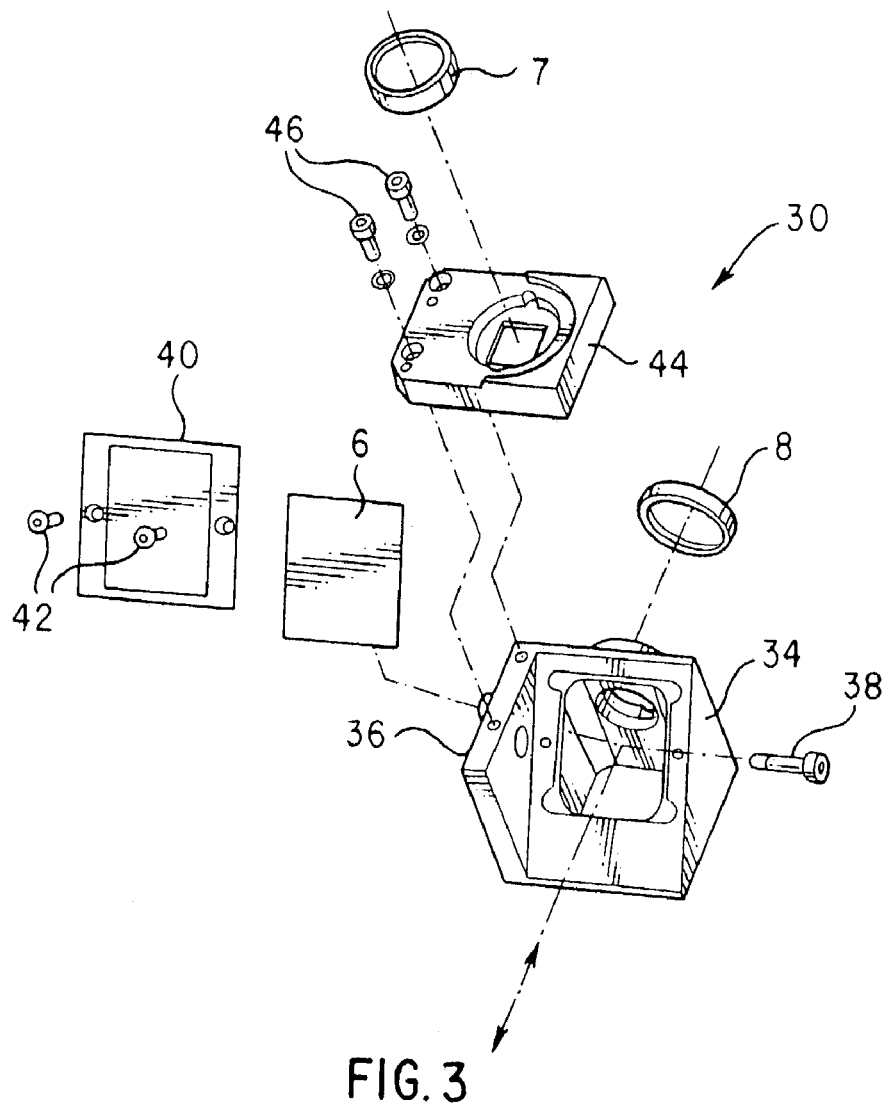
FIG. 3 is an exploded perspective of a module shown in FIG. 2.

In an example (FIG. 3), and according to various embodiments, each module can include a mounting block 34 with a flange 36 that can be affixable to the housing with a single screw 38. The beam splitter 6 can be held at 45° in the block with a frame 40 and screws 42. The emission filter 8 can mount, for example, with glue, into the block. The excitation filter 7 can be similarly mounted into a mounting member 44 that can be held by screws 46 to the block. With the module in place, the instrument can be closed up with a side plate 47 that can be screwed on. Positioning pins (not shown) ensure repeatable alignment. The replacement module can include the same mounting block and associated components, with the beam splitter and filters replaced.

According to various embodiments, the detector lens 9 (FIG. 1) can be cooperative with the vial lenses 2b and the field lens 3 to focus the individual beams on the detector 10. The lens can be large aperture, low distortion, and minimum vignetting.

According to various embodiments, the detector preferably can be an array detector, for example, a charge injection device (CID) or, preferably, a charge coupled device (CCD). A conventional video camera containing a CCD detector, the detector lens and associated electronics for the detector can be suitable, such as an Electrim model 1000L which includes 751 active pixels horizontal and 242 (non-interlaced) active pixels vertical. This camera can include a circuit board that can directly interface to a computer ISA bus. No frame grabber circuitry is required with such a camera. Essentially any other digital imaging device or subsystem can be used or adapted that can be capable of taking still or freeze-frame images for post processing in a computer.

According to various embodiments, a detector with a multiplicity of photoreceptors (pixels) 78 can be preferable if there is a plurality of vials. The detector can provide separate monitoring of each vial. In another embodiment, a scanning device can be used with a single photodetector, for example, by scanning the folding mirror and using a small aperture to the detector. A simple device such as a photomultiplier can be used, if there is only one vial. A CCD can receive light for a selected integration period and, after analog/digital conversion, can read out digital signal data at a level accumulated in this period. The integration can be effectively controlled by an electronic shutter. A frame transfer circuit can be desirable. Signal data can be generated for each pixel receiving the individual beams of emitted light from the vials.

According to various embodiments, the instrument can include a fluorescent reference member 4 that can emit a reference light in response to the excitation beam. The reference member can be formed of a plurality of reference emitters, for example, 6, each emitting a reference beam of different intensity in response to the excitation beam. The range of these intensities can approximate the range of intensities expected from the marker dye in the vials; for example, each segment can be separated in brightness by about a factor of 2.5. The reference member can be disposed to receive a portion of the excitation beam from the beam splitter. A good location for the reference member can be adjacent to the field lens, so that the optical paths associated with the member approximate those of the vials. Most of the reference light can pass back through the beam splitter as a reference beam to the detector. The detector pixels can receive the emission beam to generate reference signals for utilization along with the data signals in the computing of the concentration of the nucleic acid sequence.

Figure 4:
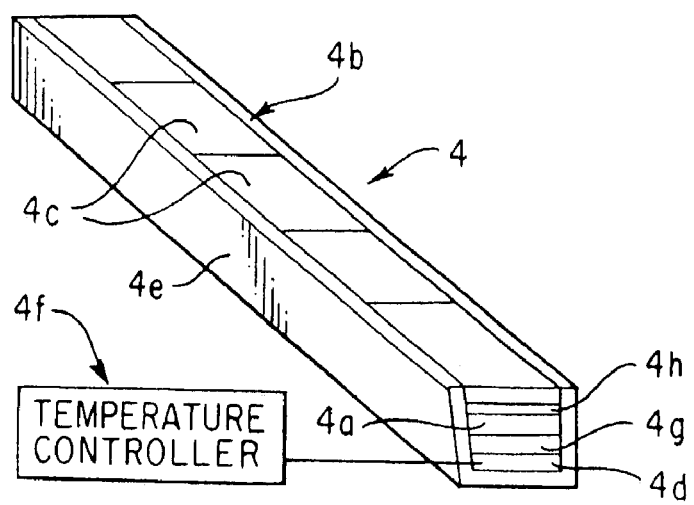
FIG. 4 is a perspective of a reference member in the optical train of FIG. 1.

According to various embodiments, the reference member 4 (FIG. 4) can include a plastic fluorescent strip 4a. The reference member 4 can include a neutral density filter 4b mounted over the fluorescent strip 4a. The reference member 4 can include an air space 4h the fluorescent strip 4a, such that a portion of the excitation beam and the reference beam can be attenuated by the neutral density filter. The neutral density filter can have a series of densities 4c to effect the plurality of reference emitters (segments), each emitting a reference beam of different intensity. A heating strip 4d and an aluminum strip 4g can be mounted in a trough 4e on the bottom thereof, as depicted in FIG. 4, to smooth the heating. The fluorescent strip can be mounted on the aluminum strip over the heating strip. To prevent heat loss, this assembly can be covered by a transparent Plexiglas window (not shown, so as to display the varying density filter). To help maintain constant fluorescence, the heating strip can be controlled to maintain the fluorescent strip at a constant temperature against the thermal cycles of the cycler block and other effects. This can be done because most fluorescent materials change in fluorescence inversely with temperature.

According to various embodiments, the computer processor 14 (FIG. 1) can be a conventional PC. The computer programming can be in conventional computer language, for example, "C". Adaptations of the programming for the present teachings can be readily recognized and achieved by those skilled in the art. The processor can selectively processes signals from pixels receiving light from the vials and the reference emitters. The processor can selectively ignore surrounding light signals. According to various embodiments, the programming can include masking to define the pixel regions of interest (ROI), for example, as disclosed in co-pending provisional patent application Ser. No. 60/092, 785 filed Jul. 14, 1998 of the present assignee. Mechanical alignment of the optics can be necessary to cooperatively focus the beams into the programmed regions of interest. The analog data signals can be fed to the processor through an analog/digital (A/D) device 15 which, for the present purpose, can be considered to be part of the processor. A saturation level can be proscribed by the detector, the A/D, the CCD dynamic range, or a combination thereof can be matched to the A/D dynamic range. A suitable range can be, for example, 8 bits of precision (256 levels). The CCD amplifier offset can be set so that the dark signal output of the CCD (with the shutter 12 closed) can be within the A/D range. The processor can instruct the detector with selected exposure time to maintain the output within the dynamic range.

Figure 5:
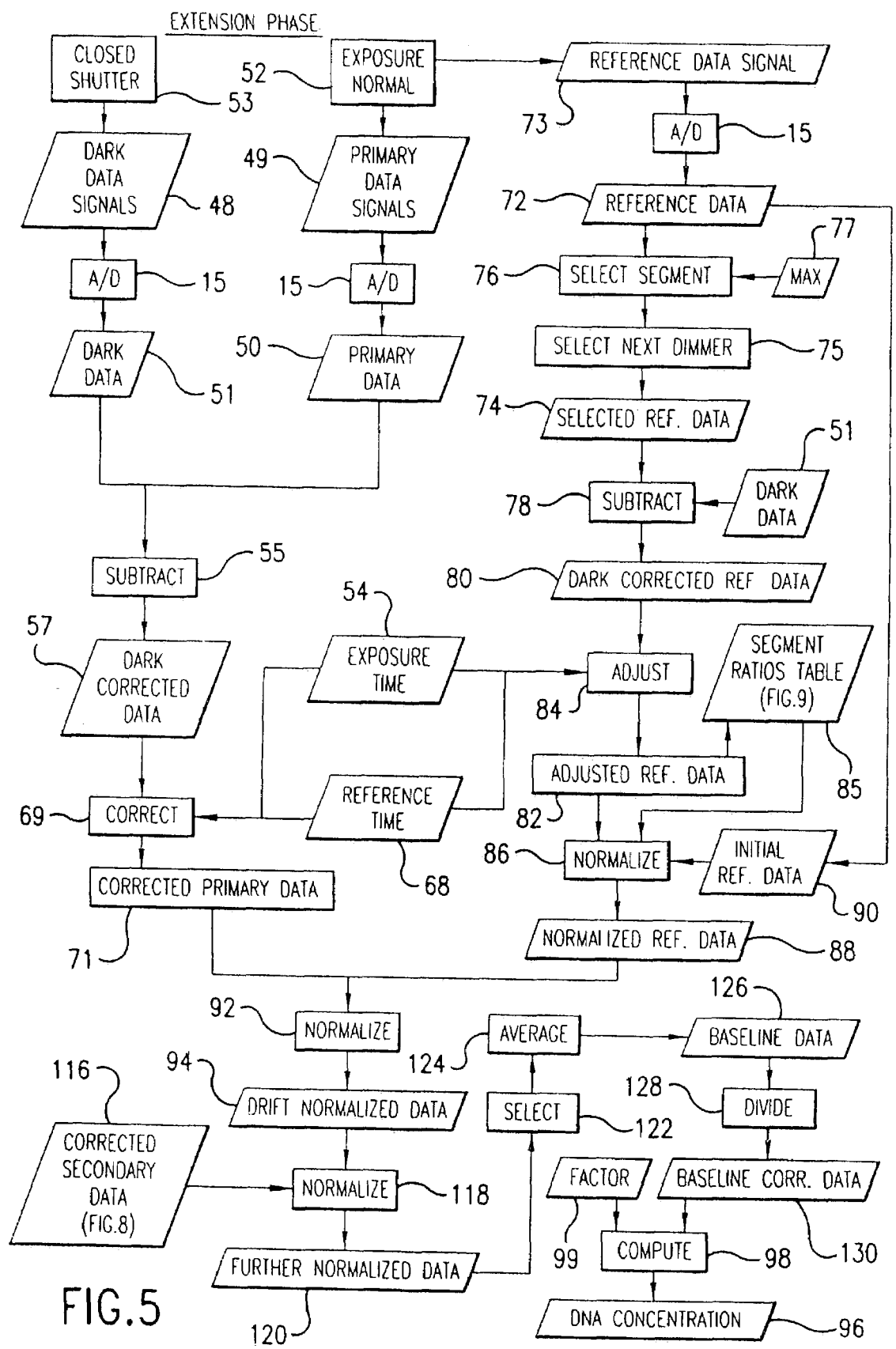
FIG. 5 is a flow chart for computing DNA concentration from data obtained with the instrument of FIG. 1.

In operation, fluorescence data can be taken from the plurality of vials (e.g. 96 regions of interest) and from the reference emitter segments, for each cycle in a nucleic acid sequence replication reaction. For PCR, the number of thermal cycles can be from about 40 cycles to about 50 cycles. Two data sets can be taken (FIG. 5) for each cycle during the extension phase of the PCR reaction at about 60° C., which can be the phase where all of the nucleic acid sequence strands have recombined into double strands. One set can be normal primary data 50 (along with reference data described below) and the other set can be dark signal data 51 with the mechanical shutter closed. Both digital data sets 50, 51 can be converted by the A/D 15 from respective analog data signals 48, 49 from the detector. The dark can be subtracted 55 from the normal, to yield dark-corrected data 57. In a simple procedure, the subtraction can be pixel by pixel. According to various embodiments, total dark for each region of interest can be subtracted from corresponding total fluorescence data. In another embodiment, multiple exposures can be collected during each exposure period, for example, 4 or 8 exposures, in order to increase the effective dynamic range of the instrument. This can be done by collecting multiple normal exposures and dark signal data for each pixel, subtracting each respective dark image from the normal data, then adding the subtracted data together to yield the primary data. This can improve the statistical validity of the image data and increases its effective dynamic range.

Figure 6:
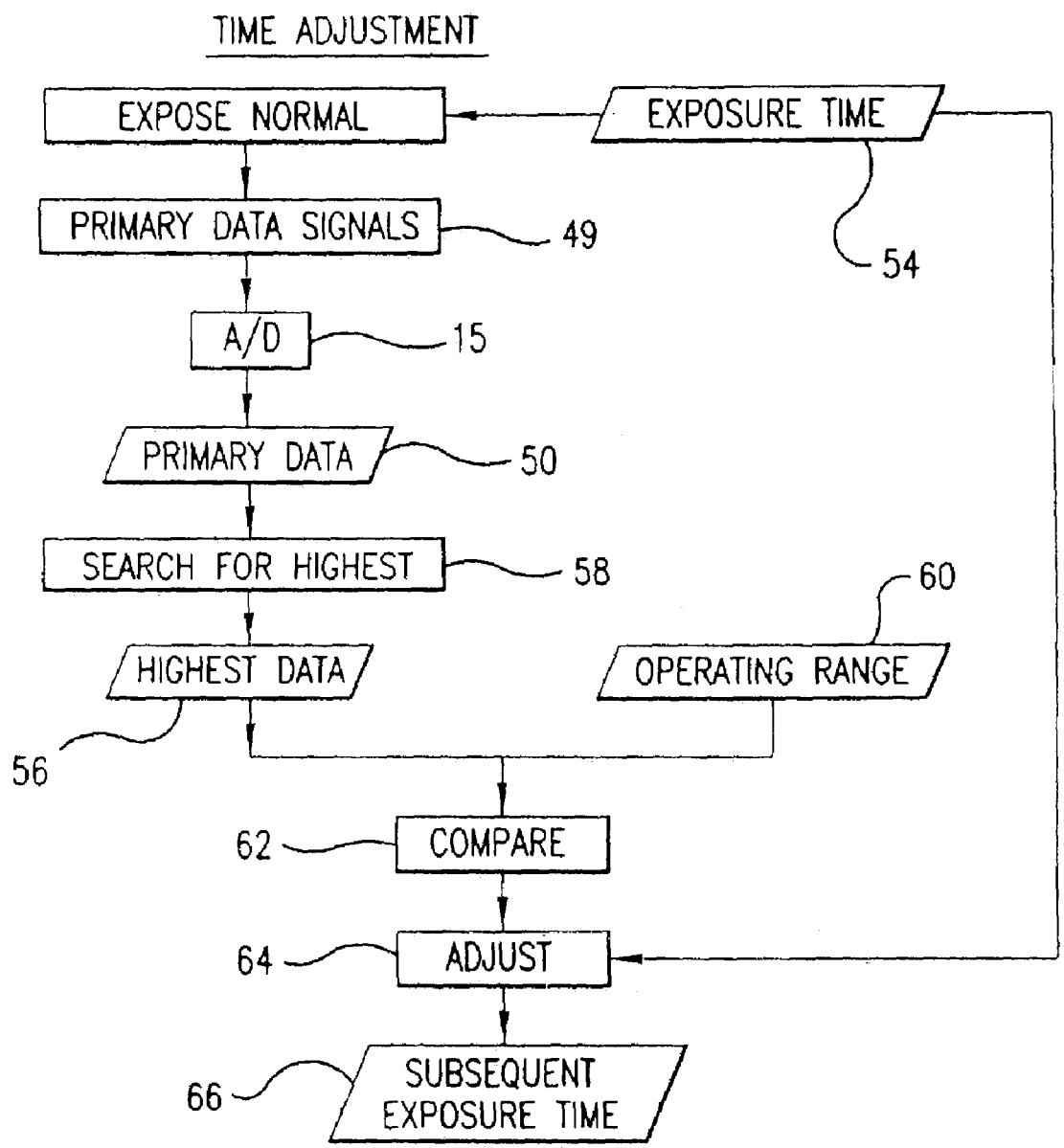
FIG. 6 is a flow chart for determining exposure time for data acquisition in operation of the instrument of FIG. 1 and for computations in the flow chart of FIG. 5.

Data can be taken simultaneously from the reference strip which includes, for example, 6 segments together with the 96 vials for a total of 102 regions of interest. According to various embodiments, the processing device can provide for automatic adjustment of the exposure time to maintain the data signals within a predetermined operating range that can be less than the saturation limit during the nucleic acid sequence replication sequence, for example, 35% to 70% of saturation. Computations for nucleic acid sequence concentration can include corrections in proportion to adjustments in exposure time (FIG. 6). Signal data 50, 51 from each exposure 52, 53 can be obtained during a previously determined exposure time 54 by totaling the pixel counts within each region of interest (ROI).

To provide the time adjustments, the highest signal data 56 can be searched out 58 from the corresponding data signals 50. The highest signal data 56 can be data from one or more of the highest pixel readings, such as the three highest contiguous pixels. It can be determined from a comparison 62 whether the highest signal data can be less than, within, or higher than the selected operating range 60. Based on such determination, the exposure time can be adjusted 64, i.e. increased, retained, or reduced, to obtain the subsequent exposure time 66. A reference time 68 (FIG. 5) can be selected which can be, for example, an initial time or a fixed standard time, for example, 1024 ms. The dark-corrected data 57 can be time-corrected 69 to yield corrected primary data 71, that can be divided by ratio of actual exposure time to the reference time. The first several cycles can be out of range, and thereafter a useful fluorescence curve can be obtained (FIG. 7).

According to various embodiments, for the reference emitter, the pixels receiving light from the reference strip 4 (FIGS. 1 and 4) reference data signals 73 can be generated and can be converted by the A/D 15 to reference data 72. Selected reference data 74 from a specific reference segment 4c (FIG. 4) can be selected 76. Reference data 74 can have the highest signal strength that can be less than a predetermined maximum 77 that, in turn, can be less than the saturation limit, for example, 70%. A next dimmer segment can be also selected 75, and the selected reference data 74 can include the data from that segment. The dark data 51 can be subtracted 78 from the reference data 74, and the dark corrected data 80 can be adjusted 84 for exposure time 54 to yield adjusted reference data 82.

Figure 9:
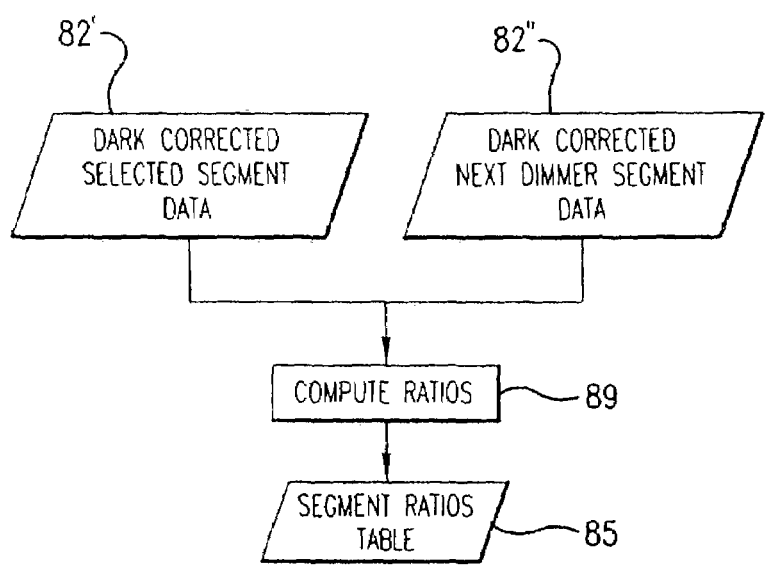
FIG. 9 is a flow chart for computing ratios between the plurality of reference emitter segments of the reference member of FIG. 4.

According to various embodiments, the data 82 can include dark corrected data 82' for the highest segment and dark corrected data 82" for the next dimmer segment (FIG. 9). The ratios of brightness between each segment can be computed 89 and can be built up over the course of data collection. Each time data is collected, the ratio between the highest and next dimmer segment can be calculated. As different optimum segments can be selected on succeeding data collections, a table of ratios 85 can be assembled. According to various embodiments, these ratios can be collected and calculated in advance. This adjusted reference data 82' (from data 82, FIG. 5) can be utilized for computing normalized reference data 88 which can be normalized 86 in real time as a ratio to reference data 90 from an initial or other selected previous cycle in the nucleic acid sequence replication sequence by working back with the ratios 85. The normalized reference data can be utilized on the corrected primary data 71 in a normalization computation 92 to provide drift normalized primary data 94 by dividing the primary data by the normalized reference data. This can correct for instrument drift during the monitoring. Nucleic acid sequence concentration 96 can then be computed 98 from a stored calibration factors 99, and can be determined by running standard known nucleic acid sequence concentrations to determine the slope and intercept of a line relating starting concentration to the starting cycle of the growth curve (FIG. 7) as taught in the aforementioned article by Higuchi and U.S. Pat. No. 5,766,889. Further normalization 118, 120 and baseline correction 122-130 are discussed below.

Figure 7:
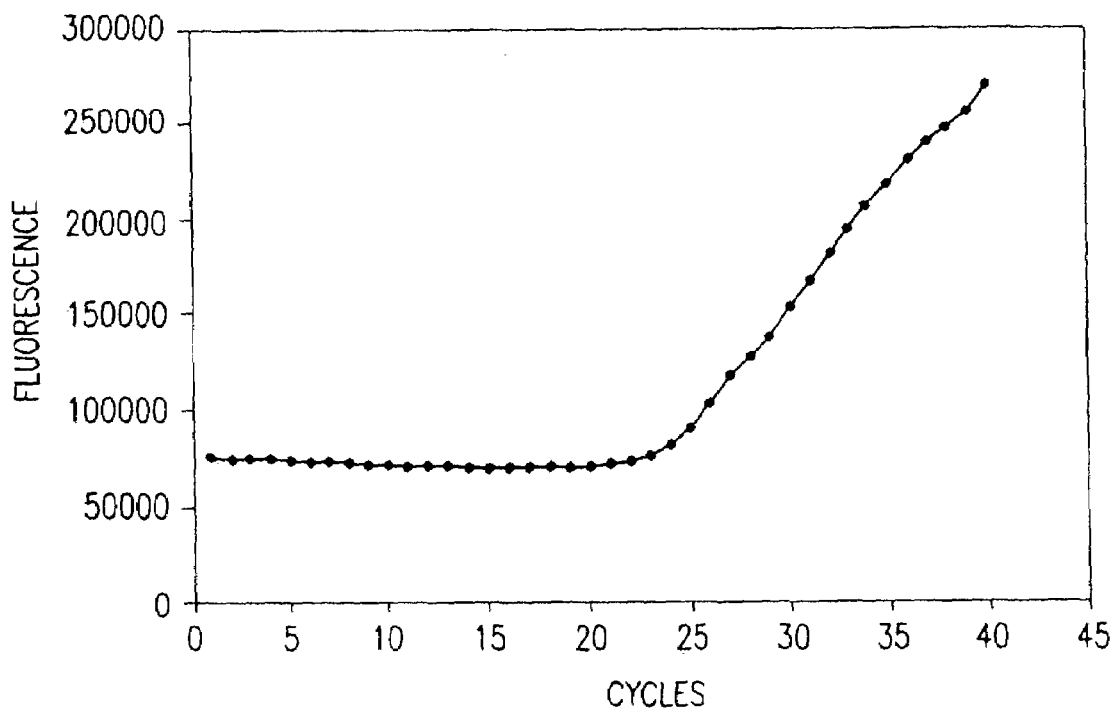
FIG. 7 is a graph of extension phase data of fluorescence vs. cycles from operation of the instrument of FIG. 1 with a PCR apparatus.

Extension phase data for a typical replication sequence could look like FIG. 7, plotted for each replication cycle. If desired, the data can be corrected for dye bleaching and/or other sample chemical effects by normalizing to sample vials containing samples with the same dye and with nucleic acid sequence amplification prevented chemically.

According to various embodiments, the sample can contain one or more types of dye molecules that serve as a "passive" reference including some fluorescence in the same wavelength range as the nucleic acid sequence binding dye. This reference dye can be a nucleic acid sequence, for example, a nucleic acid sequence labeled with Rhodamine and Fluorescein dye derivatives. A suitable reference can be Rox dye from Perkin-Elmer Applied Biosystems. These passive dye molecules do not take part in the replication reaction, so that their fluorescence can be substantially without influence from the nucleic acid sequence. Their fluorescence can remain constant during the reaction. This fluorescence can be used to normalize the fluorescence from the nucleic acid sequence binding dye with a standard concentration of passive dye included in the ingredients of at least one vial. The passive dye can be in every vial.

According to various embodiments, the source beam includes a secondary excitation frequency that can cause the passive dye to fluoresce at a secondary frequency. The passive dye can thereby emit a secondary beam directed to the detector to generate corresponding secondary data signals. The processor can be receptive of the secondary data signals for computing secondary data representative of standard concentration. These data can be used to normalize the primary data, so that the concentration of the nucleic acid sequence can be normalized to the standard concentration of passive dye after correcting computations of concentration of the nucleic acid sequence in proportion to adjustments in exposure time, and in conjunction with the normalization for drift. According to various embodiments, the secondary excitation frequency can be identical to the primary excitation frequency. The passive dye can fluoresce such that the emitted secondary beam can be substantially at the emission frequency. The primary data signals can be generated during each extension phase of cycling of the thermal cycler block when the nucleic acid sequence can be recombined and correspondingly primary dye emission can be maximized. The secondary data signals can be generated during each denature phase of cycling of the thermal cycler block when the nucleic acid sequence can be denatured and correspondingly primary dye emission can be minimized. Thus data signals for the primary phase can be substantially representative of the nucleic acid sequence concentration, and data signals for the secondary phase can be substantially representative of the standard concentration of passive dye.

According to various embodiments, the dark and normal data can be taken for the vial samples and the reference strip, and the dark can be subtracted from the normal fluorescence data. This dark and normal data set can be taken during the extension phase of the replication reaction at about 60° C., which can be the phase where all of the nucleic acid sequence strands have recombined into double strands. During this phase, the fluorescence from the nucleic acid sequence binding dye can be maximized, and the fluorescence from the passive reference molecules can be superimposed but can be much smaller. A separate dark and normal data set can be taken during the high temperature (about 95° C.) denaturing phase, during which the nucleic acid sequence can be denatured or split into single strands. During this phase, the fluorescence of the nucleic acid sequence binding dye can be minimized, and can be almost non-existent, because the nucleic acid sequence is not double stranded and the fluorescence of the dyes used can have a large decrease in fluorescence with increased temperature. Therefore, the denaturing phase images substantially can contain reference fluorescence from the passive reference molecules. The dark-corrected reference (denaturing) data set, after correction for measured temperature dependence, can be subtracted from the dark-corrected nucleic acid sequence binding dye data set, or can be deemed insignificant for the normal data set.

According to various embodiments, the passive reference dye labeled molecules can be imaged by taking the additional images, for each replication or amplification cycle, using a separate optical band pass filter that rejects wavelengths emitted by the nucleic acid sequence binding dye while accepting wavelengths from the passive reference dye. This data can be functionally equivalent to the denature data.

Figure 8:
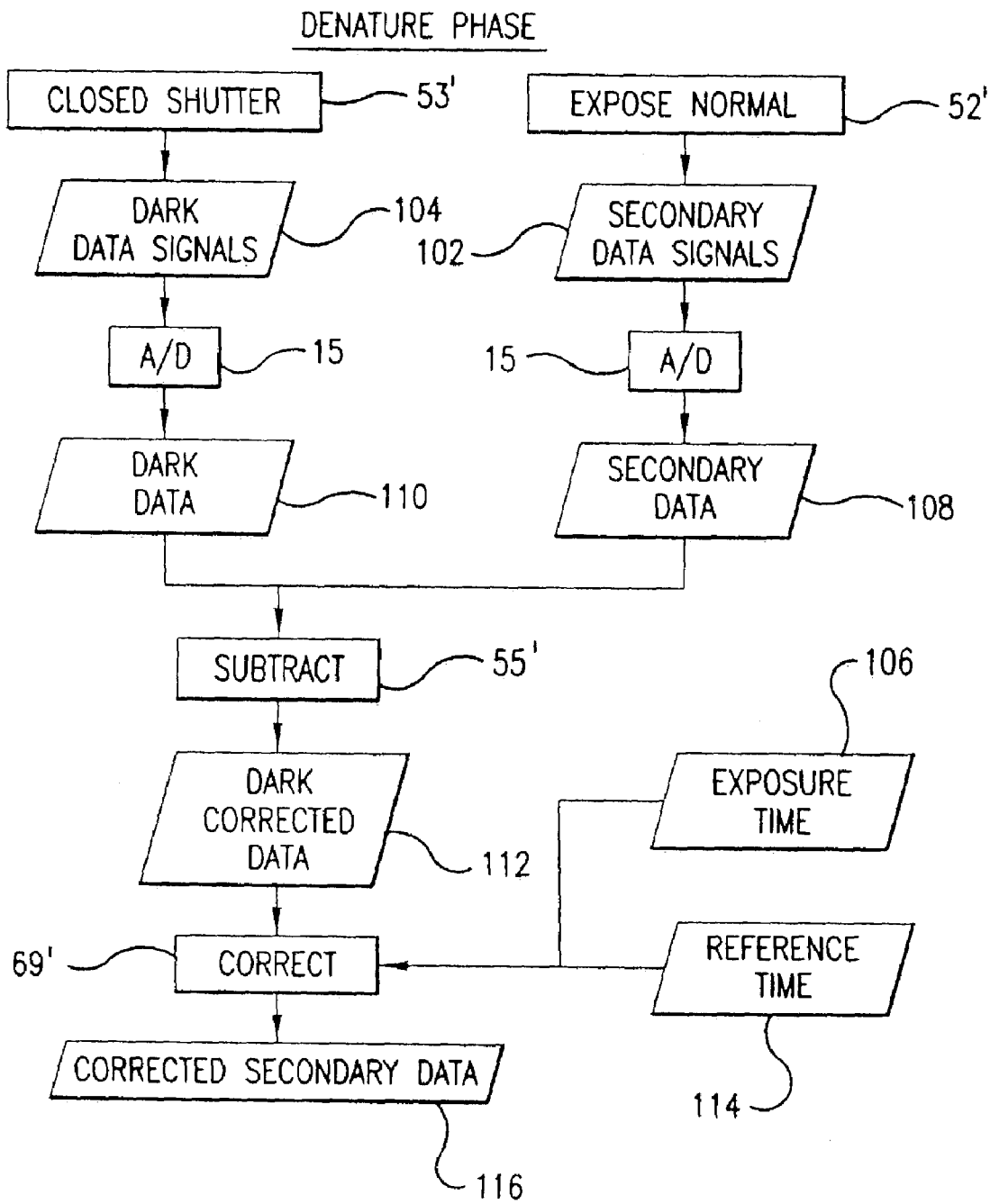
FIG. 8 is a flow chart for computing secondary data for computations in the flow chart of FIG. 5.

Illustrating operation for the denature phase (FIG. 8), respective normal and dark data signals 102, 104 can be obtained in the same manner as for the primary data, with normal exposure 52' and closed shutter 53'. Exposure time 106 can be the same as for an adjacent extension phase in the sequence, or can be determined from a previous denature phase run (as described with respect to FIG. 7), or can be a predetermined suitable time for all denature phases in the sequence. The A/D 15 can convert the signals to secondary data 108 and dark data 110. The dark can be subtracted 55' from the secondary to yield dark-corrected data 112 which can be further corrected 69' with a reference time 114 and the actual exposure time 106 that can yield corrected secondary data 116.

The extension cycle, drift normalized primary data 94 then can be normalized 118 by dividing by the average of a selected number of cycles, for example, 10, for the denature phase corrected secondary data 116 that can produce further normalized fluorescence data or further normalized data 120, which can remove sample well to well non-uniformity effects. Cycle by cycle division can be used in place of an average. According to various embodiments, the secondary data can be applied to the corrected primary data 71 before or after drift normalization. Baseline samples can be selected 122 and can be averaged 124 to produce baseline data 126. The further normalized data 120 can be then divided 128 by the baseline data to yield baseline corrected data 130. These baseline samples can be selected so as to be before the PCR growth exceeds the nearly horizontal base line portion of the curve in FIG. 7. Selected baseline cycles can be, for example, cycles 6 through 15. After further normalization 118, the further normalized data 118 can be used to compute 98 a DNA concentration 96. The trend of these same baseline samples, for example, least squares regression line, can be subtracted from the normalized extension cycle data, to produce data that can include a flat base line at zero. This data set can then be processed using established or other desired amplification methods to calculate the amount of starting copies of an nucleic acid sequence. A simple procedure can be to extrapolate for the inflection point at the transition from flat to rising. A more sophisticated procedure is described in the aforementioned U.S. Pat. No. 5,766,889.

According to various embodiments, the data can be used for various purposes, for example, quantitative monitoring of the reaction, determination of replicated nucleic acid sequence concentration, or determination of the starting amount. The instrument also be used simply to display whether replication is taking place during a sequence, or has taken place, for example, with or without normalizations and other corrections.

Various embodiments of the teachings are described herein. The teachings are not limited to the specific embodiments described, but encompass equivalent features and methods as known to one of ordinary skill in the art. Other embodiments will be apparent to those skilled in the art from consideration of the present specification and practice of the teachings disclosed herein. It is intended that the present specification and examples be considered as exemplary only.

What is claimed is:

1. An optical instrument comprising:
   an excitation light source that provides a plurality of different excitation wavelength ranges;
   at least one reaction region retaining at least one respective sample comprising a plurality of different dyes, each dye having a different respective excitation wavelength range relative to the other dyes of the plurality, the plurality of different dyes being capable of emitting emission beams of different respective wavelength ranges along an emission beam path, wherein the different excitation wavelength ranges provided by the excitation light source correspond to the different respective excitation wavelength ranges of the plurality of different dyes;
   a multi-notch beam splitter disposed along an excitation beam path between the excitation light source and the at least one reaction region, and disposed along the emission beam path, wherein the multi-notch beam splitter is configured to reflect one of (1) the plurality of different excitation wavelength ranges provided by the excitation light source and (2) the plurality of emission beams of different respective wavelength ranges, and to the pass the other of (1) and (2);
   a detector arranged along the emission beam path to detect the emission beams of the different respective wavelength ranges and generate a data signal corresponding to the emission beams;
   a processing device, operatively connected to the detector, the processing device adjusting exposure conditions of the detector to maintain the data signal within a predetermined operating range; and
   a controller for controlling the temperature of a sample in the at least one reaction region.

2. The instrument of claim 1, wherein the at least one reaction region comprises a plurality of reaction regions.

3. The instrument of claim 1, further comprising a Fresnel lens disposed along an excitation beam path between the excitation light source and the at least one reaction region.

4. The instrument of claim 1, further comprising a fold mirror disposed along an excitation beam path between the excitation light source and the at least one reaction region.

5. The instrument of claim 1, further comprising a dichroic mirror disposed along an excitation beam path between the excitation light source and the at least one reaction region.

6. The instrument of claim 1, wherein the multi-notch bean splitter is a Rugate filter.

7. A method comprising:
   generating excitation beams that provide a plurality of different excitation wavelength ranges;
   passing the excitation beams through a multi-notch beam splitter to form filtered excitation beams;
   directing the filtered excitation beams at, at least one reaction region retaining at least one respective sample comprising a plurality of different dyes, each dye having a different respective excitation wavelength range relative to the other dyes of the plurality, the plurality of different dyes being capable of emitting emission beams of different respective wavelength ranges;
   causing the at least one respective sample retained in the at least one reaction region to emit emission beams of different respective wavelength ranges wherein the different excitation wavelength ranges provided by the excitation beams correspond to the different respective excitation wavelength ranges of the plurality of different dyes;
   directing the emission beams through the multi-notch beam splitter and toward a detector;
   detecting the emission beams of different respective wavelengths emitted from the at least one respective sample;
   generating a data signal corresponding to the detected emission beams;
   adjusting exposure conditions of the detector to maintain the data signal within a predetermined operating range; and
   controlling the temperature of the at least one respective sample, during the detecting.

8. The method of claim 7, wherein the at least one reaction region comprises a plurality of reactions regions, the at least one respective sample comprises a plurality of respective samples, and each of the plurality of reaction regions retains a respective one of the plurality of respective samples.

9. The method of claim 7, further comprising passing at least one of the excitation beams and the filtered excitation beams through a Fresnel lens.

10. The method of claim 7, further comprising passing the emission beams through a Fresnel lens.

11. The method of claim 7, further comprising reflecting at least one of the excitation beams and the filtered excitation beams with a fold mirror.

12. The method of claim 7, wherein the reaction region is a well.

13. The method of claim 7, further comprising directing at least one of the excitation beams and the filtered excitation beams toward a dichroic mirror.

14. An instrument comprising:
   an excitation light source that provides a plurality of different excitation wavelength ranges;
   at least one reaction well retaining at least one respective sample comprising a plurality of different dyes, each dye having a different respective excitation wavelength range relative to the other dyes of the plurality, the plurality of different dyes being capable of emitting emission beams of different respective wavelength ranges along an emission beam path, wherein the different excitation wavelength ranges provided by the excitation light source correspond to the different respective excitation wavelength ranges of the plurality of different dyes;

a detector disposed along the emission beam path and capable of detecting emission beams of the different respective wavelength ranges emitted from the at least one reaction well and generating a data signal corresponding to the emission beams;

a processing device, operatively connected to the detector, the processing device adjusting exposure conditions of the detector to maintain the data signal within a predetermined operating range;

a multi-notch beam splitter spaced along the emission beam path between the at least one reaction well and the detector and configured to (1) reflect the plurality of emission beams of different respective wavelength ranges and pass the plurality of different respective excitation wavelength ranges, or (2) pass the plurality of emission beams of different respective wavelength ranges and reflect the plurality of different respective excitation wavelength ranges; and a controller for controlling the temperature of a sample in the at least one reaction well.

15. The instrument of claim 14, further comprising a Fresnel lens disposed along the emission beam path between the at least one reaction well and the detector.

16. The instrument of claim 14, further comprising a dichroic mirror disposed along the emission beam path between the at least one reaction well and the detector.

17. The instrument of claim 14, further comprising a fold mirror disposed along the emission beam path between the at least one reaction well and the detector.

18. The instrument of claim 14, further comprising a focusing lens disposed along the emission beam path between the at least one reaction well and the detector.

19. The instrument of claim 14, wherein the multi-notch beam splitter is a Rugate filter.

20. A method comprising:

generating excitation beams that provide a plurality of different excitation wavelength ranges;

directing the excitation beams through a multi-notch beam splitter and at, at least one reaction well retaining at least one respective sample comprising a plurality of different dyes, each dye having a different respective excitation wavelength range relative to the other dyes of the plurality, the plurality of different dyes being capable of emitting emission beams of different respective wavelength ranges;

causing the at least one respective sample to emit emission beams of different respective wavelength ranges, wherein the different excitation wavelength ranges provided by the excitation beams correspond to the different respective excitation wavelength ranges of the plurality of different dyes;

passing the emission beams of the different respective wavelength ranges through the multi-notch beam splitter to form filtered emission beams;

directing the filtered emission beams toward a detection region;

detecting the filtered emission beams emitted from the at least one respective sample;

generating a signal corresponding to the detected filtered emission beams;

adjusting exposure conditions of the detection region to maintain the data signal within a predetermined operating range; and controlling the temperature of the at least one respective sample, during the detecting.

21. The method of claim 20, further comprising reflecting the emission beams with a fold mirror.

22. The method of claim 20, further comprising passing at least one of the emission beams and the filtered emission beams through a dichroic mirror.

23. The method of claim 20, further comprising passing at least one of the emission beams and the filtered emission beams through a Fresnel lens.

24. A method comprising:

generating excitation beams that provide a plurality of different excitation wavelength ranges;

directing the excitation beams through a multi-notch beam splitter and at, at least one reaction region retaining at least one respective sample comprising a plurality of different dyes, each dye having a different respective excitation wavelength range relative to the other dyes of the plurality, the plurality of different dyes being capable of emitting emission beams of different respective wavelength ranges;

causing the at least one respective sample to undergo a nucleic acid amplification reaction:

causing the at least one sample to emit emission beams of different respective wavelength ranges, wherein the different excitation wavelength ranges provided by the excitation beams correspond to the different respective excitation wavelength ranges of the plurality of different dyes;

passing the emission beams of different respective wavelength ranges through the multi-notch beam splitter to form filtered emission beams;

directing the filtered emission beans toward a detection region;

detecting the filtered emission beams emitted from the at least one respective sample;

generating a signal corresponding to the detected filtered emission beams;

adjusting exposure conditions of the detection region to maintain the data signal within a predetermined operating range; and controlling the temperature of the at least one respective sample, during the detecting.

25. The method of claim 24, further comprising reflecting the emission beams with a fold mirror.

26. The method of claim 24, further comprising passing at least one of the emission beams and the filtered emission beams through a dichroic mirror.

27. The method of claim 24, further comprising passing at least one of the emission beams and the filtered emission beams through a Fresnel lens.

28. The method of claim 24, wherein the at least one reaction region comprises a plurality of reaction regions.

* * * * *